United States Patent [19]

Boller et al.

[11] Patent Number: 4,462,923
[45] Date of Patent: Jul. 31, 1984

[54] DISUBSTITUTED PYRIMIDINES

[75] Inventors: Arthur Boller, Binningen; Martin Schadt, Seltisberg; Alois Villiger, Basel, all of Switzerland

[73] Assignee: Hoffmann-La Roche Inc., Nutley, N.J.

[21] Appl. No.: 309,421

[22] Filed: Oct. 7, 1981

[30] Foreign Application Priority Data

Oct. 14, 1980 [CH] Switzerland .......................... 7653/80

[51] Int. Cl.$^3$ .......................... C09K 3/34; G02F 1/13; C07D 239/26
[52] U.S. Cl. .......................... 252/299.61; 252/299.63; 350/350 R; 544/242
[58] Field of Search .................... 544/242; 252/299.61, 252/299.63; 350/350 R

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,130,502 | 12/1978 | Eidenschink et al. | 252/299.63 |
| 4,273,929 | 6/1981 | Boller et al. | 252/299.1 |
| 4,309,539 | 1/1982 | Boller et al. | 252/299.61 |
| 4,335,011 | 6/1982 | Sethofer | 252/299.61 |
| 4,344,856 | 8/1982 | Demus et al. | 252/299.61 |
| 4,348,298 | 9/1982 | Zaschke et al. | 252/299.61 |
| 4,358,589 | 11/1982 | Schubert et al. | 252/299.61 |
| 4,364,838 | 12/1982 | Boller et al. | 252/299.61 |

FOREIGN PATENT DOCUMENTS

| | | | |
|---|---|---|---|
| 36711 | 9/1981 | European Pat. Off. | 252/299.61 |
| 56501 | 7/1982 | European Pat. Off. | 252/299.61 |
| 2257588 | 6/1973 | Fed. Rep. of Germany | 252/299.61 |
| 2846409 | 6/1979 | Fed. Rep. of Germany | 252/299.61 |
| 2835492 | 2/1980 | Fed. Rep. of Germany | 252/299.61 |
| 3014912 | 11/1980 | Fed. Rep. of Germany | 252/299.61 |
| 144409 | 10/1980 | German Democratic Rep. | 252/299.61 |
| 145913 | 1/1981 | German Democratic Rep. | 252/299.61 |
| 2014130 | 8/1979 | United Kingdom | 252/299.61 |
| 2025449 | 1/1980 | United Kingdom | 252/299.61 |

OTHER PUBLICATIONS

Gray, G. W., et al., Mol. Cryst. Liq. Cryst., vol. 53, pp. 147-166, (1979).
Gray, G. W., Mol. Cryst. Liq. Cryst., vol. 63, pp. 3-18, (1981).
Schubert, H., Wiss. Z Halle XIX '70M, H. 5, S.1-18.
Nash, J. A., et al., Mol. Cryst. Liq. Cryst., vol. 25, pp. 299-321, (1974).
Villiger, A., et al., Z. Naturforsch., vol. 346, pp. 1535-1541, (1979).
Schubert, H., et al., J. Prakt. Chemie., vol. 312, pp. 494-506, (1970).
Zaschke, H., et al., J. Prakt. Chemie., vol. 315, pp. 1113-1120, (1973).
Zaschke, H., J. Prakt. Chemie., vol. 317, pp. 617-630, (1975).
Zaschke, H. Z. Chemie, vol. 17, pp. 63-64 (1977).
Demus, A., et al., Mol. Cryst. Liq. Cryst, vol. 15, pp. 161-174 (1971).
Boller, A., et al., Mol. Cryst. Liq. Cryst., vol. 42, pp. 215-231, (1977).
Osman, M. A., et al., Mol. Cryst. Liq. Cryst., vol, 56 (Lett.) No. 4, pp. 105-109, (1979).
Bradshaw, M. J., et al., Mol. Cryst. Liq. Cryst., vol. 72 (Lett.), pp. 35-42, (1981).

*Primary Examiner*—Teddy S. Gron
*Attorney, Agent, or Firm*—Jon S. Saxe; Bernard S. Leon; George W. Johnston

[57] ABSTRACT

Pyrimidines of the formula:

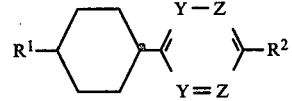

Wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl; where each alkyl denotes either a straight chain alkyl group of 1 to 12 carbon atoms or a branched chain alkyl group of the formula $C_2H_5$—$CH(CH_3)$—$(CH_2)_n$, n is 1, 2 or 3; with the proviso that the compound contains at most only one of said branched chain alkyl group and with the further proviso that the sum of the carbon atoms in all of the alkyl groups within the compound is at most 14 are described. Liquid crystalline mixtures comprising Compound I as well as their use in electro-optical devices also are disclosed.

88 Claims, No Drawings

DISUBSTITUTED PYRIMIDINES

BACKGROUND OF THE INVENTION

1. Field of the Invention

This invention relates to liquid crystalline compounds and mixtures.

2. Description of the State of the Art

In an electric field, the molecules of liquid crystalline compounds and mixtures which possess a positive anisotropy of the dielectric constants (i.e., $\epsilon_\parallel > \epsilon_\perp$) are oriented with their longitudinal axis parallel to the field direction. $\epsilon_\parallel$ signifies the dielectric constant along the longitudinal axis of the molecule and $\epsilon_\perp$ signifies the dielectric constant perpendicular thereto.

This dielectric field effect is utilized in the interaction between the liquid crystalline molecules and guest molecules (guest-host interaction) described by J. H. Heilmeier and L. A. Zanoni [Applied Physics Letter 13, 91 (1968)]. Another application of the dielectric field effect is the electro-optical rotation cell discovered by M. Schadt and W. Helfrich [Applied Physics Letters 18 (1971)]. A further example is the Kerr cell described in Molecular Crystals and Liquid Crystals 17, 355 (1972).

The above electro-optical rotation cell includes a condenser-like structure having transparent electrode plates, the dielectric of which is formed from nematic liquid crystal material with $\epsilon_\parallel > \epsilon_\perp$. The longitudinal axes of the liquid crystal molecules are arranged in twisted or helical form between the plates in the fieldless state. The twisting structure is determined by the given wall orientation of the molecules. After applying an electric potential to the condenser plates, the molecules adjust themselves with their longitudinal axes in the field direction, i.e., perpendicular to the surface of the plates, so that linear polarized light no longer rotates in the dielectric (the liquid crystal is uniaxially perpendicular to the surface of the plates). After removing the electric potential, the molecules return to their prior orientation. This reversible effect on the molecules can be used to electrically control the optical transmissivity of the condenser. To achieve an optimal transition between these two orientations, the threshold potential of the compounds or mixtures is adjusted to the driving potential of the rotation cell. The driving potential of such a "light rotation cell" is dependent on the battery potential and the control circuit used. It becomes desirable to utilize liquid crystalline mixtures having low threshold potentials.

Further, a mixture of nematic liquid crystals with positive anisotropy and cholesteric substances (or generally soluble, optically active substances provided the total mixture remains liquid crystalline) undergoes a phase transition upon application of an electric field. This phase change effect is reversible and makes it possible to have high switching speeds of electro-optical devices which operate with such mixtures.

It also is known that liquid crystalline mixtures with low viscosities have short response times.

We have invented liquid crystalline compounds and mixtures which advantageously possess low threshold potentials and viscosities.

SUMMARY OF THE INVENTION

The invention relates to pyrimidines of the formula:

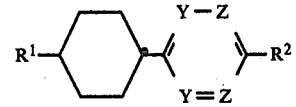

wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl; where alkyl denotes either a straight chain alkyl group of 1 to 12 carbon atoms or a branched chain alkyl group of the formula $C_2H_5$—$CH(CH_3)$—$(CH_2)_n$, n is 1, 2 or 3.

The pyrimidines contain at most only one of the branched chain alkyl groups and all the alkyl groups within Compound I at most contain 14 carbon atoms.

The inventive compounds are useful in electro-optical apparatuses and possess especially low threshold voltages as well as low viscosities.

The invention further is concerned with liquid crystal compounds, mixtures, processes, uses and apparatuses as described below.

DETAILED DESCRIPTION OF THE INVENTION

The present invention relates to trans-(4-alkylcyclohexyl)pyrimidines of the formula:

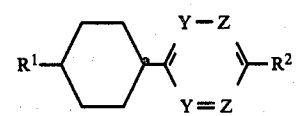

wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl, where each alkyl denotes either a straight chain alkyl group of 1 to 12 carbon atoms or a branched chain alkyl group of formula $C_2H_5$—$CH(CH_3)$—$(CH_2)_n$, n is 1, 2 or 3. The pyrimidines contain at most only one of such branched chain alkyl groups and the sum of the carbon atoms in all of the alkyl groups within the compound is at most 14.

Most of the compounds within formula I exhibit liquid crystalline properties. Illustratively optically active compounds within formula I contain a branched chain alkyl group and generally exhibit a cholesteric and/or smectic phase. The remaining compounds of formula I exhibit a nematic and/or smectic phase.

Compounds of formula I in which Y is =C—, Z is nitrogen and $R^2$ is cyano possess a high positive anisotropy of the dielectric constants. The remaining compounds of formula I possess a smaller anisotropy of the dielectric constants.

The compounds of the invention (expecially those in which $R^2$ signifies alkyl) have low viscosity. Such compounds therefore improve the response times of liquid crystalline mixtures. Further, compounds of formula I wherein Y is =CH—, Z is nitrogen and $R^2$ is cyano can be used to reduce the threshold potentials of mixtures. Moreover, some of the inventive compounds advantageously have a large mesophase range, especially compared with known dialkyl compounds. They are colorless and exhibit a high stability towards chemical influences and UV-radiation.

Unless otherwise stated, "alkyl" denotes a straight chain alkyl group of 1 to 12 carbon atoms or a branched chain alkyl group of 1 to 12 carbon atoms. Exemplary straight chain alkyl groups are methyl, ethyl, propyl, butyl, pentyl, hexyl, heptyl, octyl, nonyl, decyl, undecyl and dodecyl. Exemplary branched chain alkyl groups are isopropyl, isobutyl, sec-butyl, tert-butyl, 2-methylbutyl and isopentyl. Lower alkyl denotes straight chain and branched alkyl groups of 1 to 5 carbon atoms.

The compounds of formula I contain alkyl moieties. In Compound I, $R^1$ is alkyl and $R^2$, inter alia, is alkyl, p-alkylphenyl or trans-4-alkylcyclohexyl. The alkyl moieties in the various $R^1$ and $R^2$ substituents have a specific definition which constitutes a subgroup within the above definition for the term "alkyl". In particular, each of these alkyl moieties in Compound I denotes either a straight chain alkyl group of 1 to 12 carbon atoms or a branched chain alkyl group of the formula: $C_2H_5$—$CH(CH_3)(CH_2)_n$—, where n is 1, 2 or 3. Such branched chain alkyl groups are 2-methylbutyl, 3-methylpentyl and 4-methylhexyl.

Compound I, however, can only contain at most one of such branched chain alkyl groups. More specifically, in compounds of formula I which contain two alkyl groups (i.e., $R^1$ is alkyl and $R^2$ is alkyl, p-alkylphenyl or trans-4-alkylcyclohexyl), at least one of these alkyl moieties is a straight chain alkyl group of 1 to 12 carbon atoms. The other alkyl moiety is also a straight chain alkyl group of 1 to 12 carbon atoms or one of such branched chain alkyl groups.

Additionally, when Compound I contains two alkyl moieties, the sum of the carbon atoms in the alkyl moieties is at most 14.

The term "alkoxy" denotes alkyloxy groups in which "alkyl" is as previously defined.

The term "aromatic" means a phenyl ring.

The wavy line symbol (∼) in the formulas indicates that the substituents is in the α (below the plane of the formula) or β position (above the plane).

The dotted line symbol ( - - - ) in the formulas means that one of the bonds is a double bond.

In an aspect of the invention, there are disclosed trans-(4-alkylcyclohexyl)-pyrimidines of formula I wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl, where alkyl is a straight chain alkyl group of 1 to 12 carbon atoms, or the alkyl group in one of the substituents for $R^1$ or $R^2$ also is a branched chain alkyl group of the formula $C_2H_5$—$CH(CH_3)$—$(CH_2)_n$—, n is 1, 2 or 3, and the sum of the carbon atoms in the alkyl groups present in the compound is at most 14.

In a preferred embodiment of Compound I, Y is =CH—, Z is nitrogen and $R^2$ is p-alkylphenyl or cyano. In other preferred compounds of formula I, Y is nitrogen, Z is =CH— and $R^2$ is alkyl.

In the substituents for $R^1$ and $R^2$ of formula I which contain alkyl (i.e., $R^1$ is alkyl, $R^2$ is alkyl, p-alkylphenyl or trans-4-alkylcyclohexyl), the preferred alkyl groups are straight chain alkyl groups of 2 to 7 carbon atoms.

In an embodiment of Compound I, Y is nitrogen; Z is =CH—; $R^1$ is alkyl and $R^2$ is cyano, alkyl, p-alkylphenyl or trans-4-alkylcyclohexyl, where each alkyl denotes a straight chain alkyl group of 2 to 7 carbon atoms. The sum of the carbon atoms in all the alkyl groups within the compound is at most 14.

In another embodiment of Compound I, Z is nitrogen; Y is =CH—, $R^1$ is alkyl and $R^2$ is cyano, alkyl, p-alkylphenyl or trans-4-alkylcyclohexyl, where each alkyl denotes a straight chain alkyl group of 2 to 7 carbon atoms. The sum of the carbon atoms in all of the alkyl groups within the compound is at most 14.

In an additional embodiment of Compound I, Z is nitrogen; Y is =CH—; $R^1$ is alkyl; and $R^2$ is p-alkylphenyl or cyano. Each alkyl denotes a straight chain alkyl group of 2 to 7 carbon atoms and the sum of the carbon atoms in all of the alkyl groups within the compound is at most 14.

The following are preferred compounds of formula I:
Trans-5-(4-methylcyclohexyl)-2-pyrimidinecarbonitrile,
trans-5-(4-ethylcyclohexyl)-2-pyrimidinecarbonitrile,
trans-5-(4-propylcyclohexyl)-2-pyrimidinecarbonitrile,
trans-5-(4-butylcyclohexyl)-2-pyrimidinecarbonitrile,
trans-5-(4-pentylcyclohexyl)-2-pyrimidinecarbonitrile,
trans-5-(4-hexylcyclohexyl)-2-pyrimidinecarbonitrile,
trans-5-(4-heptylcyclohexyl)-2-pyrimidinecarbonitrile,
trans-2-(4-methylcyclohexyl)-5-pyrimidinecarbonitrile,
trans-2-(4-ethylcyclohexyl)-5-pyrimidinecarbonitrile,
trans-2-(4-propylcyclohexyl)-5-pyrimidinecarbonitrile,
trans-2-(4-butylcyclohexyl)-5-pyrimidinecarbonitrile,
trans-2-(4-pentylcyclohexyl)-5-pyrimidinecarbonitrile,
trans-2-(4-hexylcyclohexyl)-5-pyrimidinecarbonitrile,
trans-2-(4-heptylcyclohexyl)-5-pyrimidinecarbonitrile,
trans-2-(4-ethylcyclohexyl)-5-pentylpyrimidine,
trans-2-(4-propylcyclohexyl)-5-propylpyrimidine,
trans-2-(4-propylcyclohexyl)-5-butylpyrimidine,
trans-2-(4-propylcyclohexyl)-5-pentylpyrimidine,
trans-2-(4-propylcyclohexyl)-5-heptylpyrimidine,
trans-2-(4-butylcyclohexyl)-5-propylpyrimidine,
trans-2-(4-butylcyclohexyl)-5-pentylpyrimidine,
trans-2-(4-butylcyclohexyl)-5-heptylpyrimidine,
trans-2-(4-pentylcyclohexyl)-5-propylpyrimidine,
trans-2-(4-pentylcyclohexyl)-5-butylpyrimidine,
trans-2-(4-pentylcyclohexyl)-5-pentylpyrimidine,
trans-2-(4-pentylcyclohexyl)-5-hexylpyrimidine,
trans-2-(4-pentylcyclohexyl)-5-heptylpyrimidine,
trans-2-(4-hexylcyclohexyl)-5-propylpyrimidine,
trans-2-(4-hexylcyclohexyl)-5-butylpyrimidine,
trans-2-(4-hexylcyclohexyl)-5-pentylpyrimidine,
trans-2-(4-heptylcyclohexyl)-5-ethylpyrimidine,
trans-2-(4-heptylcyclohexyl)-5-propylpyrimidine,
trans-2-(4-heptylcyclohexyl)-5-pentylpyrimidine,
trans-2-(4-heptylcyclohexyl)-5-heptylpyrimidine,
trans-5-(4-ethylcyclohexyl)-2-pentylpyrimidine,
trans-5-(4-propylcyclohexyl)-2-propylpyrimidine,
trans-5-(4-propylcyclohexyl)-2-butylpyrimidine,
trans-5-(4-propylcyclohexyl)-2-pentylpyrimidine,
trans-5-(4-propylcyclohexyl)-2-heptylpyrimidine,
trans-5-(4-butylcyclohexyl)-2-pentylpyrimidine,
trans-5-(4-pentylcyclohexyl)-2-propylpyrimidine,
trans-5-(4-pentylcyclohexyl)-2-butylpyrimidine,
trans-5-(4-pentylcyclohexyl)-2-pentylpyrimidine,
trans-5-(4-hexylcyclohexyl)-2-propylpyrimidine,
trans-5-(4-hexylcyclohexyl)-2-pentylpyrimidine,
trans-5-(4-heptylcyclohexyl)-2-ethylpyrimidine,
trans-5-(4-heptylcyclohexyl)-2-propylpyrimidine,
trans-5-(4-heptylcyclohexyl)-2-butylpyrimidine,
trans-5-(4-heptylcyclohexyl)-2-pentylpyrimidine,
trans-5-(4-methylcyclohexyl)-2-(p-propylphenyl)pyrimidine,
trans-5-(4-methylcyclohexyl)-2-(p-pentylphenyl)pyrimidine,
trans-5-(4-ethylcyclohexyl)-2-(p-propylphenyl)pyrimidine, trans-5-(4-ethylcyclohexyl)-2-(p-butylphenyl)pyrimidine,
trans-5-(4-ethylcyclohexyl)-2-(p-pentylphenyl)pyrimidine,
trans-5-(4-ethylcyclohexyl)-2-(p-heptylphenyl)pyrimidine,
trans-5-(4-propylcyclohexyl)-2-(p-propylphenyl)pyrimidine,
trans-5-(4-propylcyclohexyl)-2-(p-butylphenyl)pyrimidine,
trans-5-(4-propylcyclohexyl)-2-(p-pentylphenyl)pyrimidine,
trans-5-(4-butylcyclohexyl)-2-(p-pentylphenyl)pyrimidine,
trans-5-(4-pentylcyclohexyl)-2-(p-propylphenyl)pyrimidine,
trans-5-(4-pentylcyclohexyl)-2-(p-butylphenyl)pyrimidine,
trans-5-(4-pentylcyclohexyl)-2-(p-pentylphenyl)pyrimidine,
trans-5-(4-hexylcyclohexyl)-2-(p-propylphenyl)pyrimidine,
trans-5-(4-heptylcyclohexyl)-2-(p-ethylphenyl)pyrimidine,
trans-5-(4-heptylcyclohexyl)-2-(p-propylphenyl)pyrimidine,
trans-5-(4-heptylcyclohexyl)-2-(p-pentylphenyl)pyrimidine,
trans-2-(4-ethylcyclohexyl)-5-(p-propylphenyl)pyrimidine,
trans-2-(4-ethylcyclohexyl)-5-(p-pentylphenyl)pyrimidine,
trans-2-(4-propylcyclohexyl)-5-(p-propylphenyl)pyrimidine,
trans-2-(4-propylcyclohexyl)-5-(p-butylphenyl)pyrimidine,
trans-2-(4-propylcyclohexyl)-5-(p-pentylphenyl)pyrimidine,
trans-2-(4-butylcyclohexyl)-5-(p-propylphenyl)pyrimidine,
trans-2-(4-pentylcyclohexyl)-5-(p-propylphenyl)pyrimidine,
trans-2-(4-pentylcyclohexyl)-5-(p-butylphenyl)pyrimidine,
trans-2-(4-pentylcyclohexyl)-5-(p-pentylphenyl)pyrimidine,
2,5-bis(trans-4-propylcyclohexyl)pyrimidine,
5-(trans-4-propylcyclohexyl)-2-(trans-4-pentylcyclohexyl)pyrimidine,
5-(trans-4-propylcyclohexyl)-2-(trans-4-heptylcyclohexyl)pyrimidine,
5-(trans-4-pentylcyclohexyl)-2-(trans-4-propylcyclohexyl)pyrimidine,
5-(trans-4-pentylcyclohexyl)-2-(trans-4-pentylcyclohexyl)pyrimidine,
5-(trans-4-heptylcyclohexyl)-2-(trans-4-propylcyclohexyl)pyrimidine,
5-(trans-4-heptylcyclohexyl)-2-(trans-4-pentylcyclohexyl)pyrimidine,
(+)-trans-5-[4-(2-methylbutyl)cyclohexyl]-2-pyrimidinecarbonitrile,
(+)-trans-5-[4-(3-methylpentyl)cyclohexyl]-2-pyrimidinecarbonitrile,
(+)-trans-5-[4-(4-methylhexyl)cyclohexyl]-2-pyrimidinecarbonitrile,
(+)-trans-2-[4-(2-methylbutyl)cyclohexyl]-5-pyrimidinecarbonitrile,
(+)-trans-2-[4-(2-methylbutyl)cyclohexyl]-5-butylpyrimidine,
(+)-trans-2-[4-(2-methylbutyl)cyclohexyl]-5-pentylpyrimidine,
as well as the antipodes of the optically active compounds.

In accordance with the invention, Compound I can be manufactured as follows:

(a) for Compound I in which $R^2$ is alkyl, p-alkylphenyl or trans-4-alkylcyclohexyl, reacting a compound of the formula:

with an acid addition salt (preferably the hydrochloride) of a compound of the formula:

wherein one of $R^7$ and $R^9$ is trans-4-alkylcyclohexyl and the other is alkyl, p-alkylphenyl or trans-4-alkylcyclohexyl and $R^8$ is lower alkyl, in the presence of a base (preferably an alcoholate) (e.g., alkali metal alcoholates such as sodium methylate and sodium ethylate);

(b) for Compound I in which $R^2$ is cyano, dehydrating a compound of the formula:

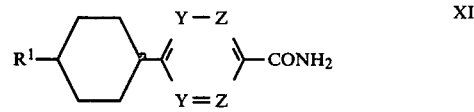

wherein Y is nitrogen and Z is =CH—, or Z is nitrogen and Y is =CH—; $R^1$ is a straight chain alkyl group of 1 to 12 carbon atoms or a branched chain alkyl group of formula $C_2H_5$—$CH(CH_3)$—$(CH_2)_n$, n is 1, 2 or 3; wherein $R^1$, Y and Z are as above;

(c) for Compound I in which Y is =CH—, Z is nitrogen and $R^2$ is cyano, dehydrating a compound of the formula:

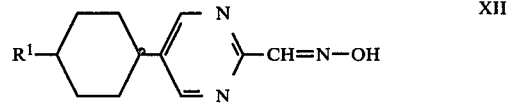

wherein $R^1$ is as above.

The reaction of Compound IX with an acid addition salt of Compound X conveniently is carried out in water or an organic solvent (e.g., an alcohol such as methanol, ethanol, ethyleneglycol and the like) in the presence of a base. Methanol and ethanol are preferred solvents. The acid addition salts of Compound X can be salts of hydrochloric acid, hydrobromic acid, sulphuric acid, p-toluenesulphonic acid and the like. However, the hydrochloride of the compounds of formula X preferably is used. Alkali metal alcoholates, (especially sodium methylate and sodium ethylate) are the preferred bases. The lower alkyl group $R^8$ conveniently is an alkyl group of 1 to 5 carbon atoms such as methyl, ethyl, propyl, isopropyl and the like, and preferably is methyl and ethyl. The reaction temperature and pressure are not critical. Conveniently, the reaction is conducted at atmospheric pressure and a temperature between about room temperature (23° C.) and about the reflux temperature, preferably at about room temperature.

The dehydration of Compound XI can be carried out using any suitable dehydrating agent. Illustratively, such agents include phosphorus oxychloride, phosphorus pentoxide, thionyl chloride, acetic anhydride and, especially, benzenesulphonyl chloride and the like. The dehydration can be carried out in an inert organic solvent (such as a hydrocarbon or halogenated hydrocarbon) if necessary in the presence of a base (such as sodium acetate, pyridine or triethylamine). It can, however, also be carried out in the absence of an organic solvent. If desired, the base, insofar as it is liquid at the reaction temperature, can also serve as the solvent. The reaction temperature preferably lies between about 50° C. and about the reflux temperature of the reaction mixture. The pressure is not critical and the reaction advantageously is carried out at atmospheric pressure.

The dehydration of Compound XII can be carried out in an analogous manner to the dehydration of Compound XI using a suitable dehydrating agent and, if desired, using an inert organic solvent and/or a base. Illustratively, the reaction can be carried out using phosphorus oxychloride, acetic anhydride and anhydrous sodium acetate in glacial acetic acid or, preferably, benzenesulphonyl chloride in pyridine. The reaction is preferably conducted at a temperature between about 50° C. and about the reflux temperature of the reaction mixture. The pressure is not critical and the reaction is advantageously carried out at atmospheric pressure.

Compounds IX and X are known or can be made from known compounds [Z. Naturforsch. 33 b, 433 (1978) and 34 b, 1535 (1979)].

The preparation of the starting materials of formulas XI and XII is illustrated by the following Reaction Schemes 1 and 2 in which $R^1$ is as above.

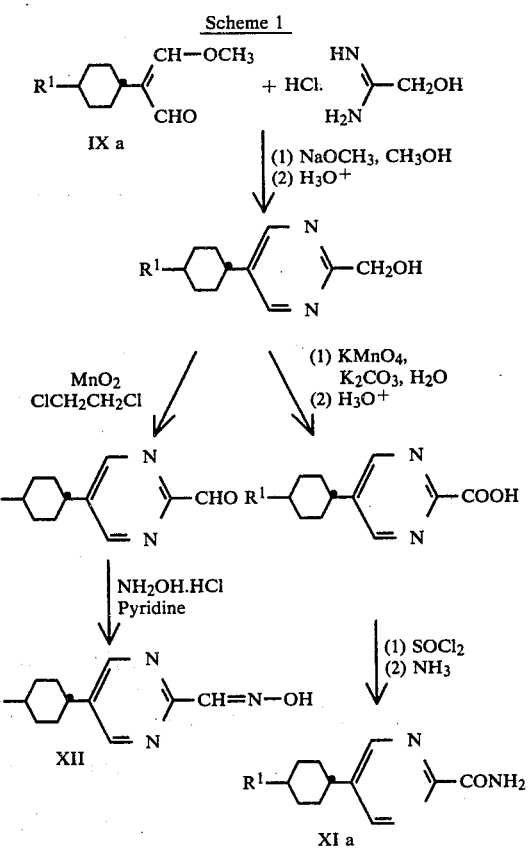

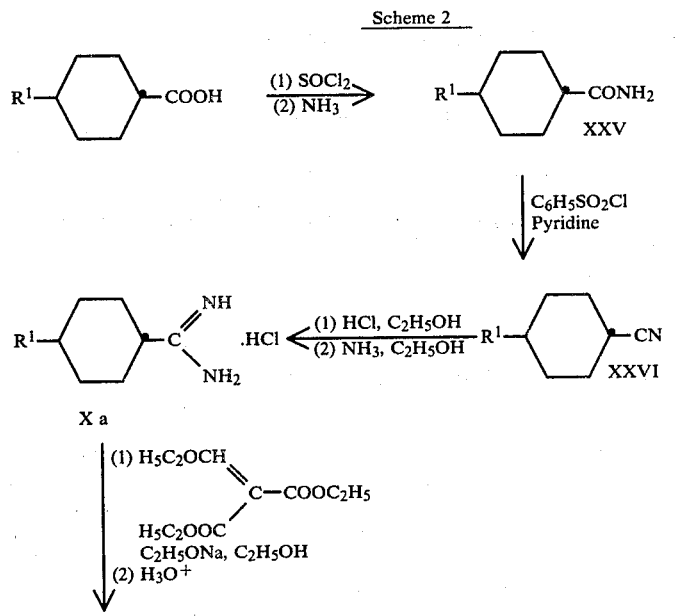

Scheme 2

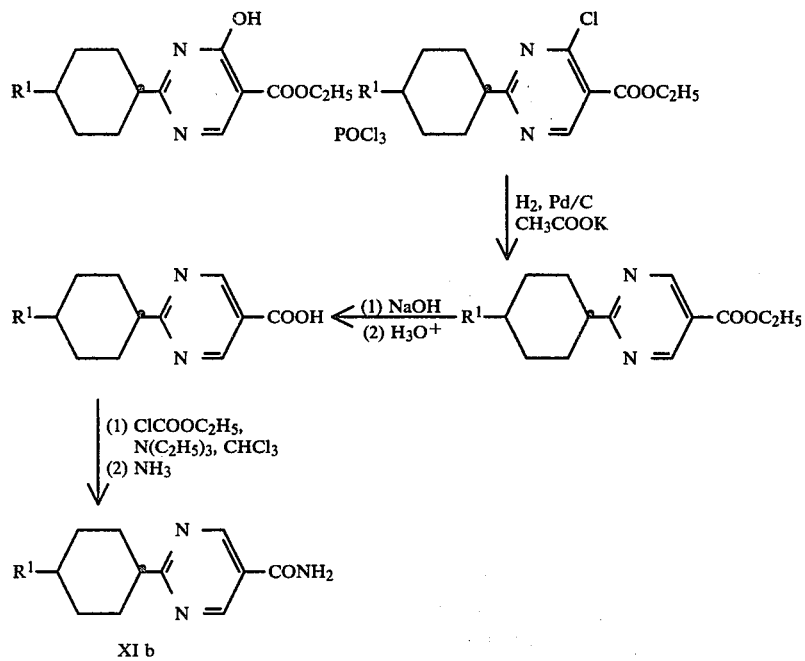

The starting materials for Schemes 1 and 2 or analogs of these compounds are described in Z. Naturforsch, 34 b, 1535 (1979) and in Mol. Cryst. Liq. Cryst. 37, 189 (1976) or 42, 215 (1977). The compounds, thus, are known or can be made from known compounds by conventional procedures.

Compound XXVI is novel and also forms an object of the present invention. Illustratively, such compounds can be used as doping agents in liquid crystal mixtures. They can be prepared by dehydrating Compound XXV in an analogous manner to dehydrating Compound XI as described earlier.

The present invention also concerns liquid crystalline mixtures. The compounds of formula I are valuable especially as components of liquid crystalline mixtures. The inventive compounds preferably are used for manufacturing liquid crystalline mixtures having positive anisotropy of the dielectric constants.

The compounds of formula I can be mixed with other liquid crystalline and/or non-liquid crystalline substances to form such liquid crystalline mixtures. Illustratively, such substances can be selected from classes of Schiff's bases, azobenzenes, azoxybenzenes, phenyl benzoates, cyclohexanecarboxylic acid phenyl esters, biphenyls, terphenyl, phenylcyclohexanes, cinnamic acid derivatives, phenylpyrimidines, diphenylpyrimidines, phenyldioxanes, cyclohexylphenylpyrimidines and the like. Such substances are known to a person skilled in the art. See, e.g., German Offenlegungsschriften Nos. 2,306,738 (U.S. Pat. No. 3,927,064); 2,306,739 (U.S. Pat. No. 3,923,857); 2,429,093; 2,356,085 (U.S. Pat. No. 3,947,375); 2,636,684 (U.S. Pat. No. 4,130,502); 2,459,374 (U.S. Pat. No. 3,927,066); 2,547,737 (U.S. Pat. No. 3,997,536); 2,641,724 (U.S. Pat. No. 4,062,798); 2,708,276 (U.S. Pat. No. 4,180,475); and 2,811,001 (U.S. patent application Ser. No. 101,604); East German Patent Specification Nos. 139,852 and 139,867 and from European Patent Application Publication No. 0014885 (U.S. patent application Ser. No. 116,518). Many of such substances are commercially available.

The inventive liquid crystalline mixtures can include
(a) hydrogenated naphthalenes of the formula:

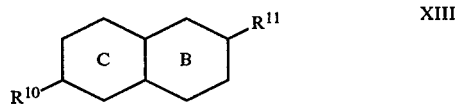

XIII wherein ring C is saturated; ring B is saturated or aromatic; $R^{10}$ is a straight chain alkyl group or alkoxy group of 1 to 11 carbon atoms; and $R^{11}$ is cyano, a straight chain alkyl group of 1 to 11 carbon atoms, or an ester group of the formula:

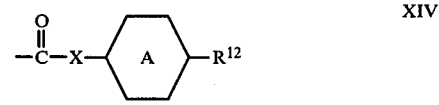

XIV wherein ring A is either aromatic and X is oxygen or sulphur and $R^{12}$ is cyano or a straight chain alkyl group or alkoxy group of 1 to 10 carbon atoms, or ring A is trans-1,4-disubstituted cyclohexane and X is oxygen and $R^{12}$ is cyano or a straight chain alkyl group of 1 to 10 carbon atoms;
with the proviso that when ring B is saturated, it is trans-linked with ring C; with the additional proviso that when ring B is saturated, $R^{11}$ may also be a straight chain alkoxy group of 1 to 11 carbon atoms; and with the further proviso that the total number of carbon atoms in the alkyl and/or alkoxy groups within the compound is at most 12; and/or
(b) benzodioxanes of the formula:

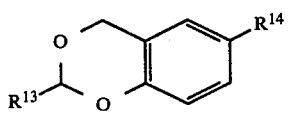  XV wherein $R^{13}$ is a straight chain alkyl group of 1 to 11 carbon atoms; $R^{14}$ is cyano, a straight chain alkyl group of 1 to 11 carbon atoms or an ester of formula XIV hereinbefore in which X, A and $R^{12}$ are as above; and the total number of carbon atoms in the alkyl and alkoxy groups within the compound is at most 12.

The compounds of formulas XIII and XV are novel. Those in which $R^{11}$ or $R^{14}$ signifies an ester group of formula XIV are to a large extent themselves liquid crystalline. The remaining compounds (i.e., the compounds of formula XIII in which $R^{11}$ signifies cyano, straight chain alkyl or straight chain alkoxy) and the compounds of formula XV in which $R^{14}$ signifies cyano or straight chain alkyl, are suitable as doping agents in liquid crystal mixtures but in general are not liquid crystalline themselves. In the case of mixtures which contain such doping agents, care must accordingly be taken that the mixtures also contain at least one compound having liquid crystalline properties in sufficient amount so that the total mixture has liquid crystalline properties.

Compound XIII can be manufactured by the following process:

(a) for Compound XIII in which $R^{11}$ is an ester group of formula XIV, esterifying a compound of the formula:

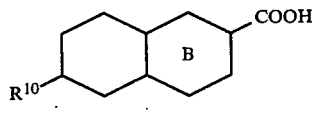  XVII wherein $R^{10}$ and B are as above;
or a reactive derivative thereof (e.g., the corresponding acid chloride) with a compound of the formula:

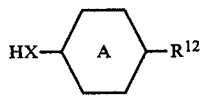  XVI wherein X, A and $R^{12}$ are as above;

(b) for Compound XIII in which $R^{11}$ is cyano, dehydrating a compound of the formula:

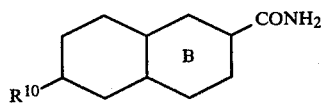  XVIII wherein $R^{10}$ and B are as above;

(c) for Compound XIII in which $R^{11}$ is a straight chain alkyl group, reacting a compound of the formula:

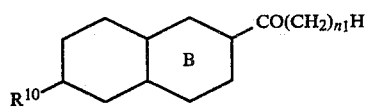  XIX wherein $n_1$ is an integer from 0 to 10 and $R^{10}$ and B are as above; with hydrazine in the presence of a base (e.g., potassium hydroxide, sodium ethylate, potassium tert.-butylate and the like);

(d) for Compound XIII in which ring B is saturated and $R^{11}$ is a straight chain alkoxy group, etherifying a compound of the formula:

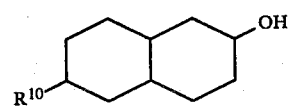  XX wherein $R^{10}$ is as above.

Compound XVI is known or can be manufactured from known compounds by conventional procedures. The preparation of Compounds XVII–XX is illustrated by the following Reaction Schemes A-C in which $R^{10}$, B and $n_1$ are as above, $n_2$ is an integer from 1 to 10.

Scheme A

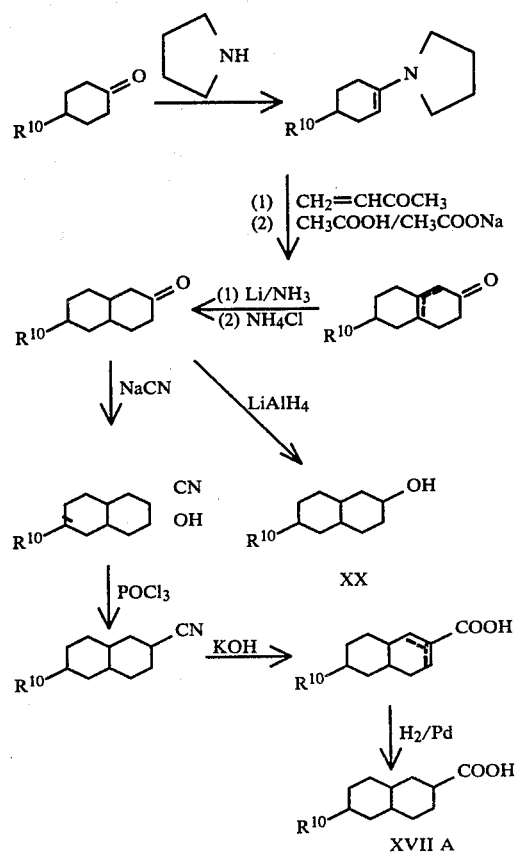

Scheme B

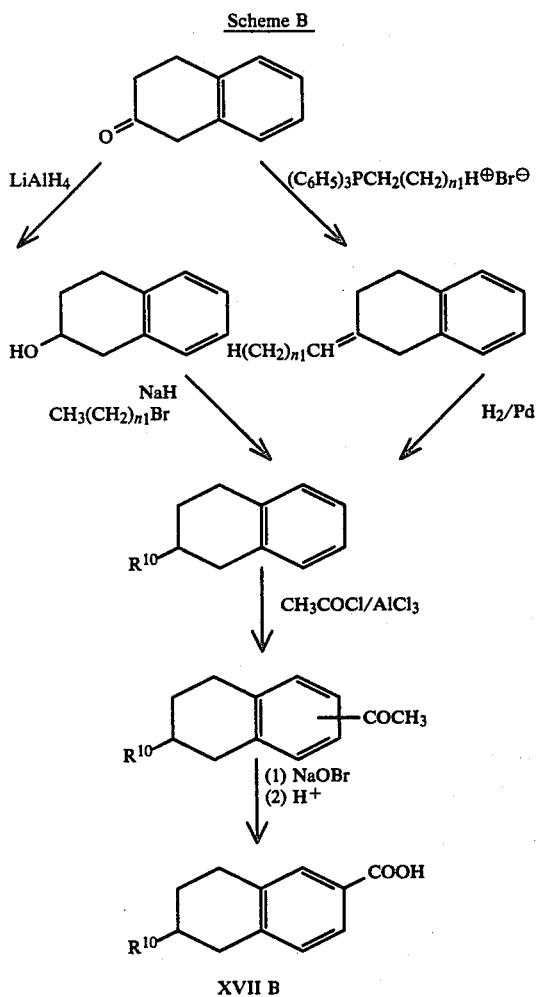

Scheme C

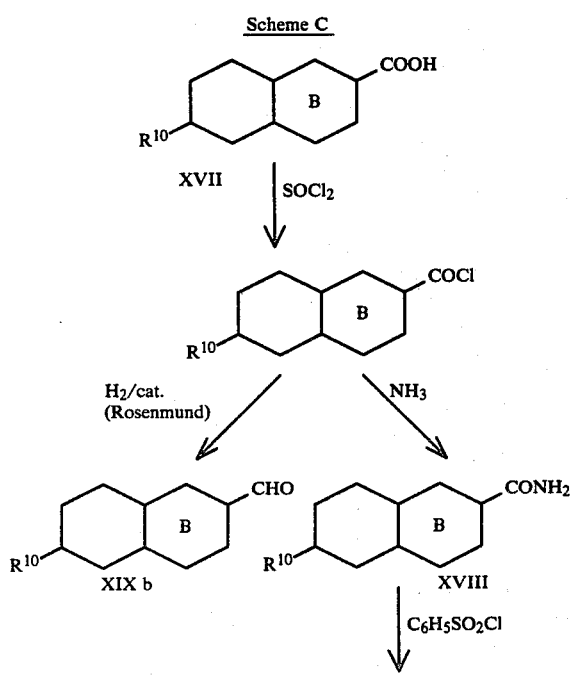

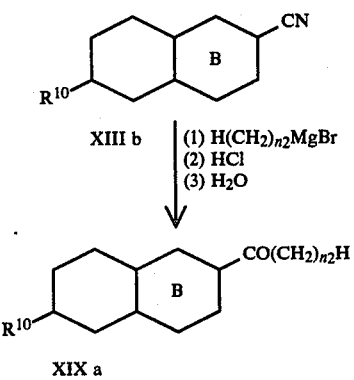

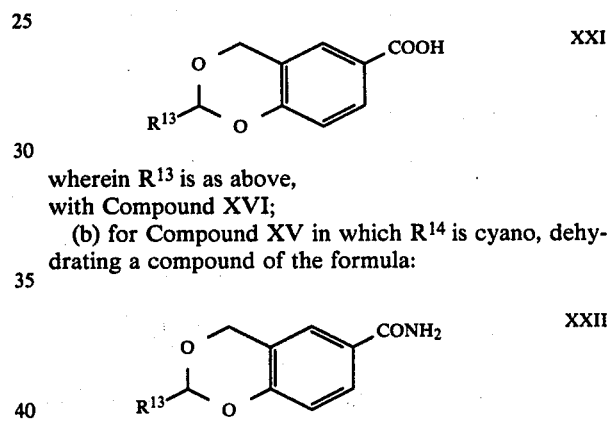

Compound XV can be manufactured by the following process:

(a) for Compound XV in which $R^{14}$ is an ester group of formula XIV, esterifying a compound of the formula:

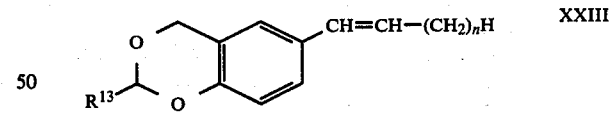

wherein $R^{13}$ is as above,
with Compound XVI;

(b) for Compound XV in which $R^{14}$ is cyano, dehydrating a compound of the formula:

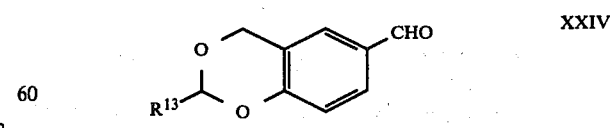

wherein $R^{13}$ is as above;

(c) for Compound XV in which $R^{14}$ is a straight chain alkyl group of 2 to 11 carbon atoms, catalytically hydrogenating a compound of the formula:

XXIII wherein n is an integer from 0 to 9 and $R^{13}$ is as above;

(d) for Compound XV in which $R^{14}$ is methyl, reacting a compound of the formula:

XXIV wherein $R^{13}$ is as above,
with hydrazine in the presence of a base (e.g., potassium hydroxide, sodium ethylate, potassium tert.-butylate and the like).

Starting materials XXI-XXIV can be prepared according to following Scheme D in which $R^{13}$ is a straight chain alkyl group of 1 to 11 carbon atoms and n is 1, 2 or 3.

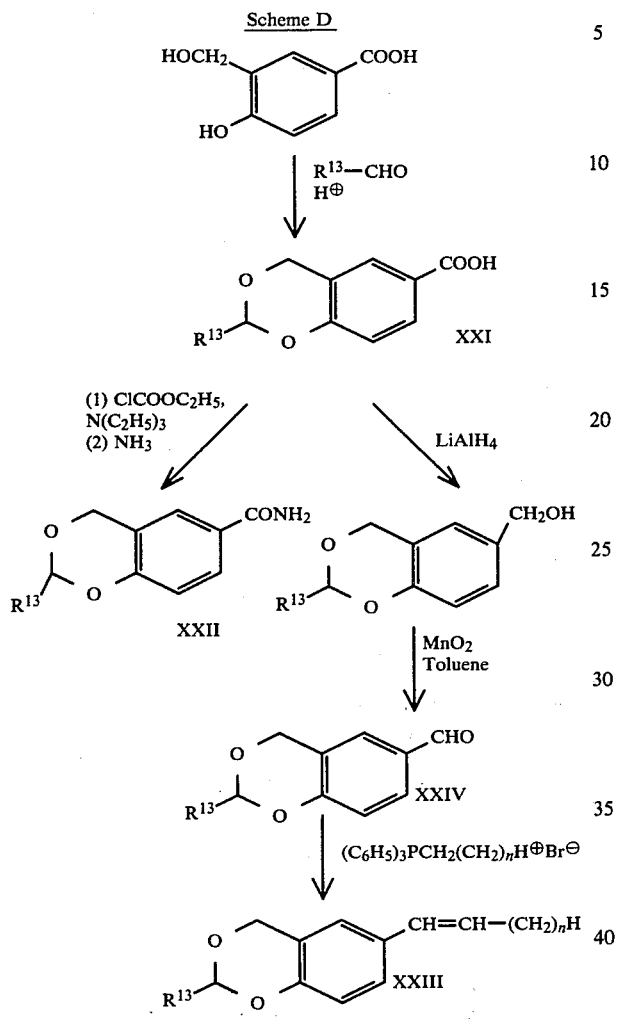

As noted above, the present invention also concerns mixtures of liquid crystalline materials containing Compound I.

In addition to one or more compounds of formula I, the inventive liquid crystal mixtures preferably include one or more of the following compounds:

(a) 4-cyanobiphenyls of the formula:

wherein $R^3$ is a straight chain alkyl or alkoxy group of 2 to 7 carbon atoms; and/or (b) trans-p-(4-alkylcyclohexyl)benzonitriles of the formula:

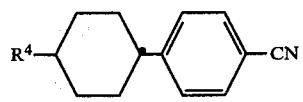

wherein $R^4$ is a straight chain alkyl group of 3 to 7 carbon atoms; and/or (c) p-(5-alkyl-2-pyrimidinyl)benzonitriles of the formula:

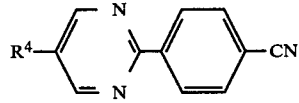

wherein $R^4$ is as above; and/or (d) p-(trans-5-alkyl-m-dioxan-2-yl)benzonitriles of the formula:

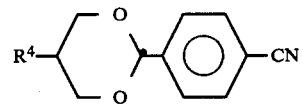

wherein $R^4$ is as above;

(e) p-alkylbenzoic acid p'-cyanophenyl esters of the formula:

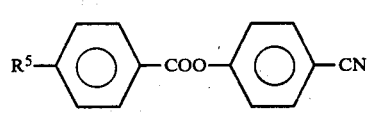

wherein $R^5$ is a straight chain alkyl group of 2 to 7 carbon atoms;

(f) trans-4-alkylcyclohexanecarboxylic acid phenyl esters of the formula:

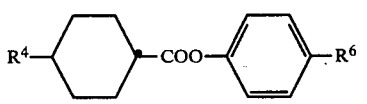

wherein $R^4$ is as above and $R^6$ is cyano or a straight chain alkoxy group of 1 to 3 carbon atoms; and/or (g) trans-p-[5-(4-alkylcyclohexyl)-2-pyrimidinyl]benzonitriles of the formula:

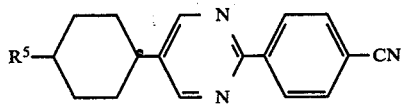

wherein $R^5$ is as above.

The weight ratio of the above components of the inventive mixture preferably corresponds to the eutectic composition. When large amounts of compounds of formula I are used, however, the total mixture possibly can be smectic. The amount of the compounds of formula I in the liquid crystal mixtures generally can be about 1 to about 40 mol percent and preferably about 5 to about 30 mol percent of the total mixture. In mixtures which contain compounds of formula I in which $R^2$ is p-alkylphenyl or trans-4-alkylcyclohexyl, the amount of such compounds generally lies between about 1 and about 20 mol percent and preferably between about 3 and about 10 mol percent of the total mixture.

The inventive liquid crystalline mixtures can contain optically active compounds. Illustratively, such compounds include optically active biphenyls, and/or dichroic coloring substances (e.g., azo, azoxy and anthraquinone coloring substances). The amount of such optically active compounds in the mixtures is determined by the desired pitch, color, extinction, solubility and the like.

The inventive mixtures containing, inter alia, Compound I and other liquid crystalline and/or non-liquid crystalline compounds can be manufactured by conventional procedures. Illustratively, a mixture of the desired components can be heated to a temperature barely above the clearing point and subsequently cooled down.

In another aspect of the invention, Compound I (which is miscible with all known liquid crystals) can be used in all customary electro-optical devices. The choice of the components of the mixture generally depends on the purpose.

An electro-optical device containing one or more compounds of the formula I can be manufactured in a known manner. Illustratively, the device can be produced by evacuating a suitable cell and introducing the inventive compound or mixture into the evacuated cell.

The invention is also concerned with all novel compounds, mixtures, processes, uses and devices as herein described.

The following non-limiting Examples illustrate the invention. Unless otherwise stated, percentages and ratios are given in volume and the temperatures are expressed in degrees Centigrade. Room temperature is 23° C. The ether is diethyl ether and the alcohol is ethanol. One bar pressure is 0.987 atmospheres.

EXAMPLE 1

Preparation of trans-5-(4-pentylcyclohexyl)-2-pyrimidinecarbonitrile 9.0 g of trans-5-(4-pentylcyclohexyl)-2-pyrimidinecarboxaldehyde are dissolved in 150 ml of pyridine under a nitrogen atmosphere, treated with 3.9 g of hydroxylamine hydrochloride and stirred at room temperature for 2 hours. Thereafter, the mixture is treated with 18.3 g of benzenesulphonyl chloride, the temperature rising to about 50° C. Subsequently, the mixture is stirred at a bath temperature of 70° C. for 6 hours, then cooled, poured into 500 ml of ice/water and 100 ml of concentrated hydrochloric acid and extracted with ether. The extract is washed with dilute hydrochloric acid, washed neutral with water, dried over sodium sulphate and evaporated. The crude product obtained is chromatographed on a column of 275 g of silica gel with hexane/20% ether. The almost pure fractions (in accordance with thin-layer chromatography) are combined and recrystallized three times from hexane. There is obtained pure trans-5-(4-pentylcyclohexyl)-2-pyrimidinecarbonitrile; m.p. 83.5° C.

The trans-5-(4-pentylcyclohexyl)-2-pyrimidinecarboxaldehyde used as the starting material can be prepared as follows:

(a) 9.1 g of 2-hydroxyacetamidine hydrochloride are suspended under a nitrogen atmosphere in a solution of 17.8 g of 3-methoxy-2-(trans-4-pentylcyclohexyl)acrolein [prepared analogously to the 3-ethoxy compound described in Z. Naturforsch, 34 b, 1535 (1979)] in 150 ml of absolute methanol. Subsequently, a sodium methylate solution, freshly prepared from 3.1 g of sodium in 75 ml of absolute methanol, is added dropwise, the mixture is stirred overnight at room temperature and then adjusted to pH 4 by adding about 3 ml of concentrated hydrochloric acid. Thereafter, the precipitate is filtered off, the filtrate is evaporated and the residue is treated with water and ether. The product is present in the organic phase and this is washed with water, dried over sodium sulphate, filtered and evaporated. The crude product obtained is chromatographed on a column of 425 g of silica gel with toluene/10% acetone. The pure fractions (in accordance with thin-layer chromatography) of trans-5-(4-pentylcyclohexyl)-2-pyrimidinecarbinol are combined and evaporated. Yield: 6.8 g.

(b) A solution of 12.0 g of trans-5-(4-pentylcyclohexyl)-2-pyrimidinecarbinol in 300 ml of ethylene chloride is treated with 21.7 g of activated manganese dioxide. The mixture is heated to boiling until starting material can no longer be observed in the thin-layer chromatogram (about 4 hours) and filtered. After evaporating the filtrate, there are obtained 9.0 g of oily, almost pure (in accordance with thin-layer chromatography) trans-5-(4-pentylcyclohexyl)-2-pyrimidinecarboxaldehyde.

The following compounds can be manufactured in an analogous manner:

Trans-5-(4-heptylcyclohexyl)-2-pyrimidinecarbonitrile; m.p. 81° C., (+)-trans-5-[4-(2-methylbutyl)cyclohexyl]-2-pyrimidinecarbonitrile; m.p. 47.5° C.

EXAMPLE 2

Preparation of trans-2-(4-propylcyclohexyl)-5-pyrimidinecarbonitrile 20.3 g of benzenesulphonyl chloride are added while stirring to a mixture of 9.45 g of trans-2-(4-propylcyclohexyl)-5-pyrimidinecarboxamide and 55 ml of pyridine. After 2 hours, the solution is poured into a mixture of 100 g of ice and 0.9 ml of half-concentrated hydrochloric acid. The precipitated product is taken up in ether and the ether extract is washed neutral with water, dried and evaporated. The crude product is purified by chromatography on 200 g of silica gel with hexane/benzene (1:1) and subsequent bulb-tube distillation at 135° C./0.05 mmHg. There is obtained trans-2-(4-propylcyclohexyl)-5-pyrimidinecarbonitrile; m.p. 74° C., cl.p 89.5° C., smectic-nematic phase transition 71.5° C. (monotropic).

The trans-2-(4-propylcyclohexyl)-5-pyrimidinecarboxamide used as the starting material can be prepared as follows:

(a) A mixture of 52.1 g of trans-4-propylcyclohexanecarboxylic acid and 200 ml of thionyl chloride is heated to boiling for 2 hours. The excess thionyl chloride is distilled off and the residue is evaporated twice with 100 ml of benzene each time. The oily acid chloride formed is dissolved in 200 ml of methylene chloride and added to 500 ml of methylene chloride into which ammonia is conducted. Ammonia is conducted into the resulting suspension for a further 3 hours and then the mixture is evaporated in vacuo. The residue is treated with water and methylene chloride, the organic phase is separated and the aqueous phase is back-extracted. The organic extracts are dried over sodium sulphate and concentrated. The crude trans-4-propylcyclohexanecarboxamide is recrystalized from acetone (m.p. 189°–191° C.). This product can be purified further by sublimation at 150° C./0.1 mmHg; m.p. 195.6°–195.9° C.

(b) 22.3 g of trans-4-propylcyclohexanecarboxamide are dissolved partly in 275 ml of pyridine. 27 g of benzenesulphonyl chloride are added dropwise within 15 minutes while stirring. Subsequently, the mixture is warmed at 55° C. for 4 hours, then cooled, poured into ice/water and subsequently extracted with ether. The extract is washed several times with 3N hydrochloric acid, then washed neutral with water, dried over sodium sulphate and concentrated. There are obtained 19.6 g of liquid trans-4-propylcyclohexanecarbonitrile; b.p. 125° C./13 mmHg (bulb-tube distillation).

(c) Dry hydrogen chloride is conducted for several hours into a solution, cooled to 0°–5° C., of 18.3 g of trans-4-propylcyclohexanecarbonitrile in 150 ml of benzene. The closed vessel is left to stand at room temperature overnight and then the contents are evaporated in vacuo. The resulting foam is treated with 300 ml of absolute ether and this suspension is stirred in a closed vessel for 1.5 hours in an ice-bath. Subsequently, the mixture is suction filtered and the residue is backwashed with a small amount of absolute ether and dried in vacuo. The very hydrolysis-sensitive imino ester hydrochloride obtained (28 g) is dissolved in 60 ml of absolute ethanol and treated while stirring with 63.7 g of a solution of ammonia in ethanol (containing 11.3 g of ammonia). The precipitate which results immediately again passes into solution after about 10 minutes. The mixture is left to stand overnight and is then evaporated. The residue is suspended in 170 ml of ether, left to stand at 0° C. for 4 hours and then suction filtered and dried. There are obtained 25.7 g of crude trans-4-propylcyclohexanecarboxamidine hydrochloride (m.p. 210°–211° C.). For purification it is recrystallized from ethanol/ether; yield 24.0 g, m.p. 214°–215° C.

(d) 23.9 g of trans-4-propylcyclohexanecarboxamidine hydrochloride and 25.2 g of diethyl ethoxymethylene-malonate are added to a sodium ethylate solution prepared from 5.4 g of sodium and 210 ml of ethanol and the mixture is diluted with 150 ml of ethanol. The mixture is stirred at room temperature for 50 minutes and at boiling temperature for 50 minutes and, after cooling, evaporated in vacuo. The viscid residue is suspended in 600 ml of water and acidified with 60 ml of glacial acetic acid. Subsequently, the suspension is stirred for 1.5 hours in an ice-bath and suction filtered. The material on the suction filter is washed with water and dried at 50° C. in vacuo over potassium hydroxide. There are obtained 33 g of ethyl trans-4-hydroxy-2-(4-propylcyclohexyl)-5-pyrimidinecarboxylate; m.p. 156°–157° C.

(e) 32.85 g of ethyl trans-4-hydroxy-2-(4-propylcyclohexyl)-5-pyrimidinecarboxylate are boiled under reflux for 3.5 hours with 210 ml of phosphorus oxychloride. After cooling, the mixture is concentrated in vacuo and evaporated twice further with 100 ml of toluene each time. The residue is chromatographed with methylene chloride on a column of 300 g of silica gel. There are obtained 31.3 g of crude ethyl trans-4-chloro-2-(4-propylcyclohexyl)-5-pyrimidinecarboxylate as a yellow oil.

(f) 31.1 g of ethyl trans-4-chloro-2-(4-propylcyclohexyl)-5-pyrimidinecarboxylate are dissolved in 350 ml of ethanol and, after adding 14.1 g of potassium acetate and 2.56 g of palladium/carbon (5% by weight), the mixture is hydrogenated at room temperature until 0.10–0.11 mol of hydrogen have been taken up. The mixture is suction filtered, back-washed with methylene chloride and evaporated in vacuo. Thereby, there are obtained 35.6 g of crude, partly crystalline ethyl trans-2-(4-propylcyclohexyl)-5-pyrimidinecarboxylate which is used in the next step without further purification.

(g) 35.6 g of crude ethyl trans-2-(4-propylcyclohexyl)-5-pyrimidinecarboxylate are treated with 62 ml of ethanol and a solution of 46.6 g of sodium hydroxide in 312 ml of water and heated to boiling for 1 hour. After cooling, the mixture is acidified with 220 ml of half-concentrated hydrochloric acid, left to stand for 1 hour in an ice-bath and then suction filtered. The material on the suction filter is washed with water and dried in vacuo at 50° C. over potassium hydroxide. For purification, the crude product is recrystallized from dioxan/water. There is obtained trans-2-(4-propylcyclohexyl)-5-pyrimidinecarboxylic acid; m.p. 184°–185.5° C.

(h) A solution of 13.85 g of trans-2-(4-propylcyclohexyl)-5-pyrimidinecarboxylic acid, 260 ml of chloroform and 7.8 ml of triethylamine is cooled to 2° C. and treated with 5.32 ml of ethyl chloroformate. The mixture is stirred at 2° C. for 15 minutes and then a strong stream of ammonia gas is conducted in for 10 minutes (while cooling with an ice-bath). The resulting suspension is stirred at 20° C. for a further 1 hour and then evaporated in vacuo. The solid residue is stirred up with 210 ml of water for 45 minutes and then filtered off under suction and dried. There are obtained 9.6 g of crude trans-2-(4-propylcyclohexyl)-5-pyrimidinecarboxamide (m.p. 234°–235° C.) which can be purified by sublimation at 175° C./0.05 mmHg; m.p. 249.3°–250.5° C.

The following compounds can be manufactured in an analogous manner:

Trans-2-(4-methylcyclohexyl)-5-pyrimidinecarbonitrile; m.p. 86° C., trans-2-(4-ethylcyclohexyl)-5-pyrimidinecarbonitrile; m.p. 82° C., trans-2-(4-butylcyclohexyl)-5-pyrimidinecarbonitrile; m.p. 60° C., smectic-nematic phase transition 85° C., cl.p. 91° C., trans-2-(4-pentylcyclohexyl)-5-pyrimidinecarbonitrile; m.p. 70° C., smectic-nematic phase transition 94° C., cl.p. 98° C., trans-4-methylcyclohexanecarbonitrile; b.p. 85°–90° C./12 mmHg, trans-4-ethylcyclohexanecarbonitrile; b.p. 105°–110° C./13 mmHg, trans-4-butylcyclohexanecarbonitrile; b.p. 80° C./0.02 mmHg.

EXAMPLE 3

Preparation of trans-5-(4-propylcyclohexyl)-2-pentylpyrimidine 6.8 g of caproic acid amidine hydrochloride are suspended in a solution of 7.4 g of 3-methoxy-2-(trans-4-propylcyclohexyl)acrolein in 50 ml of absolute methanol. Subsequently, a sodium methylate solution, freshly prepared from 1.2 g of sodium in 40 ml of absolute methanol, is added dropwise thereto. The mixture is stirred at room temperature for a further 20 hours and then adjusted to pH 5 by adding about 2 ml of concentrated hydrochloric acid. The mixture is evaporated in vacuo and the residue is treated with water and extracted with ether. The extract is washed neutral with water, dried over sodium sulphate, filtered and evaporated. The crude product is chromatographed on a column of 250 g of silica gel with hexane/20% ether. The pure fractions (in accordance with thin-layer chromatography) are combined and recrystallized from 50 ml of acetonitrile at about −20° C. There is obtained analytically pure trans-5-(4-propylcyclohexyl)-2-pentylpyrimidine; m.p. 33° C., cl.p. 48° C. (smectic).

The following compounds can be manufactured in an analogous manner:

Trans-5-(4-ethylcyclohexyl)-2-pentylpyrimidine; m.p. 24° C., cl.p. 16.5° C. (monotropic smectic),
trans-5-(4-propylcyclohexyl)-2-propylpyrimidine; m.p. 28° C., cl.p. 20° C. (monotropic smectic),
trans-5-(4-propylcyclohexyl)-2-butylpyrimidine; m.p. 29.5° C., cl.p. 31.5° C. (smectic),
trans-5-(4-pentylcyclohexyl)-2-propylpyrimidine; m.p. 34° C., cl.p. 29.5° C. (monotropic smectic),
trans-5-(4-pentylcyclohexyl)-2-butylpyrimidine; m.p. 19° C., cl.p. 40.5° C. (smectic),
trans-5-(4-pentylcyclohexyl)-2-pentylpyrimidine; m.p. 33.5° C., cl.p. 60° C. (smectic),
trans-5-(4-heptylcyclohexyl)-2-propylpyrimidine; m.p. 29.5° C., cl.p. 30° C. (smectic), monotropic nematicisotropic phase transition 29.2° C.,
trans-5-(4-heptylcyclohexyl)-2-butylpyrimidine; m.p. 32.5° C., cl.p. 40.5° C. (smectic),
trans-5-(4-heptylcyclohexyl)-2-pentylpyrimidine; m.p. 34° C., cl.p. 60° C. (smectic).

EXAMPLE 4

Preparation of trans-2-(4-pentylcyclohexyl)-5-heptylpyrimidine

In an analogous manner to that described in Example 3, a mixture of 3.8 g of 3-ethoxy-2-heptylacrolein, 4.7 g of trans-4-pentylcyclohexanecarboxamidine hydrochloride and 40 ml of absolute methanol is treated with a sodium methylate solution prepared from 0.8 g of sodium in 25 ml of absolute methanol. The reaction duration, working-up and chromatography are as described in Example 3. The pure fractions eluted in the chromatography are combined and recrystallised twice from acetonitrile at about −20° C. There is obtained analytically pure trans-2-(4-pentylcyclohexyl)-5-heptylpyrimidine; m.p. 22° C., cl.p. 40.5° C. (smectic).

The following compounds can be manufactured in an analogous manner:

Trans-2-(4-propylcyclohexyl)-5-propylpyrimidine; m.p. 25° C.,
trans-2-(4-propylcyclohexyl)-5-butylpyrimidine; m.p. 9° C.,
trans-2-(4-pentylcyclohexyl)-5-propylpyrimidine; m.p. 26° C.,
trans-2-(4-pentylcyclohexyl)-5-butylpyrimidine; m.p. 3.5° C., cl.p. −7° C. (monotropic nematic),
trans-2-(4-pentylcyclohexyl)-5-pentylpyrimidine; m.p. 17° C., cl.p. 10° C. (monotropic nematic),
trans-2-(4-heptylcyclohexyl)-5-heptylpyrimidine; m.p. 19° C., cl.p. 45° C. (smectic).

EXAMPLE 5

Preparation of trans-5-(4-propylcyclohexyl)-2-(p-pentylphenyl)-pyrimidine

In an analogous manner to that described in Example 3, a mixture of 3.0 g of 3-methoxy-2-(trans-4-propylcyclohexyl)acrolein, 3.75 g of p-pentylbenzoic acid amidine hydrochloride and 50 ml of absolute methanol is treated with a sodium methylate solution prepared from 0.5 g of sodium in 20 ml of absolute methanol. The reaction duration, working-up and chromatography are as described in Example 3. The pure fractions resulting in the chromatography are combined and recrystallised from hexane. There is obtained analytically pure trans-5-(4-propylcyclohexyl)-2-(p-pentylphenyl)pyrimidine; m.p. 93.5° C., smectic-nematic phase transition 178°–179° C., cl.p. 190° C.

The following compounds can be manufactured in an analogous manner:

Trans-5-(4-ethylcyclohexyl)-2-(p-propylphenyl)pyrimidine; m.p. 125.5° C., smectic-nematic phase transition 128.5° C., cl.p. 167° C.,
trans-5-(4-ethylcyclohexyl)-2-(p-butylphenyl)pyrimidine; m.p. 108.5° C., smectic-nematic phase transition 140° C., cl.p. 163.5° C.,
trans-5-(4-ethylcyclohexyl)-2-(p-pentylphenyl)pyrimidine; m.p. 101° C., smectic-nematic phase transition 139° C., cl.p. 167° C.,
trans-5-(4-ethylcyclohexyl)-2-(p-heptylphenyl)pyrimidine; m.p. 80° C., smectic-nematic phase transition 138.5° C., cl.p. 157° C.,
trans-5-(4-propylcyclohexyl)-2-(p-propylphenyl)-pyrimidine; m.p. 116.5° C., smectic-nematic phase transition 175° C., cl.p. 194.5° C.,
trans-5-(4-pentylcyclohexyl)-2-(p-propylphenyl)pyrimidine; m.p. 51° C., cl.p. 190° C. (smectic),
trans-5-(4-pentylcyclohexyl)-2-(p-butylphenyl)pyrimidine; m.p. 37.5° C., cl.p. 187° C. (smectic),
trans-5-(4-heptylcyclohexyl)-2-(p-ethylphenyl)pyrimidine; m.p. 68° C., smectic-nematic phase transition 179° C., cl.p. 182° C.,
trans-5-(4-heptylcyclohexyl)-2-(p-pentylphenyl)pyrimidine; m.p. 122.5° C., cl.p. 186.5° C. (smectic).

EXAMPLE 6

Preparation of trans-2-(4-pentylcyclohexyl)-5-(p-butylphenyl)pyrimidine

In an analogous manner to that described in Example 3, a mixture of 6.3 g of 3-ethoxy-2-(p-butylphenyl)acrolein, 6.6 g of trans-4-pentylcyclohexanecarboxamidine hydrochloride and 60 ml of absolute methanol is treated with a sodium methylate solution prepared from 1.1 g of sodium in 25 ml of absolute methanol. The reaction duration, working-up and chromatography are as described in Example 3. The pure fractions (in accordance with thin-layer chromatography) resulting in the chromatography are combined and recrystallized twice from hexane. There is obtained analytically pure trans-2-(4-pentylcyclohexyl)-5-(p-butylphenyl)pyrimidine; m.p. 87° C., smectic-nematic phase transition 136.5° C., cl.p. 146.5° C.

The following compound can be manufactured in an analogous manner:

Trans-2-(4-propylcyclohexyl)-5-(p-butylphenyl)pyrimidine; m.p. 98° C., smectic-nematic phase transition 130° C., cl.p. 145° C.

EXAMPLE 7

Preparation of 5-(trans-4-propylcyclohexyl)-2-(trans-4-pentylcyclohexyl)pyrimidine In an analogous manner to that described in Example 3, a mixture of 3.2 g of 3-methoxy-2-(trans-4-propylcyclohexyl)acrolein, 4.1 g of trans-4-pentylcyclohexanecarboxamidine hydrochloride and 50 ml of absolute methanol is treated with a sodium methylate solution prepared from 0.53 g of sodium in 20 ml of absolute methanol. The reaction duration, working-up and chromatography are as described in Example 3. The pure fractions (in accordance with thin-layer chromatography) resulting in the chromatography are combined and recrystallized twice from hexane. There is obtained pure 5-(trans-4-propylcyclohexyl)-2-(trans-4-pentylcyclohexyl)pyrimidine; m.p. 98° C., cl.p. 178° C. (smectic).

The following compound can be manufactured in an analogous manner:

5-(Trans-4-heptylcyclohexyl)-2-(trans-4-pentylcyclohexyl)pyrimidine; m.p. 193° C., cl.p. 190° C. (monotropic smectic).

EXAMPLE 8

Preparation of p-cyanophenyl 2-pentyl-1,2,3,4-tetrahydro-6-naphthoate 6.16 g (25 mmol) of 2-pentyl-1,2,3,4-tetrahydronaphthalene-6-carboxylic acid are boiled at reflux with 62.5 ml of thionyl chloride while excluding moisture for 2 hours. After removing the excess thionyl chloride, the acid chloride is obtained as a yellowish oil.

The acid chloride, diluted with 10 ml of absolute benzene, is added dropwise while stirring at 3°–7° C. to a solution, cooled to 3° C., of 2.99 g (25 mmol) of p-cyanophenyl in 15 ml of absolute pyridine, the mixture is left to stand overnight, then poured into a mixture of 30 g of ice and 30 ml of hydrochloric acid (1:1), exhaustively extracted with ether and the organic phases are washed once with 35 ml of ice-cold 1N sodium hydroxide and water. After drying with sodium sulphate and removing the solvent in vacuo, there is obtained a crystalline residue (8.6 g) of p-cyanophenyl 2-pentyl-1,2,3,4-tetrahydro-6-naphthoate which, for purification, is chromatographed on 230 g of silica gel. Elution with benzene/hexane (1:1) and benzene yields 8.1 g of substance which is recrystallized from acetone/hexane up to constant melting point and clearing point and dried up to constant weight in a high vacuum (0.01 mbar). There are obtained colorless crystals of p-cyanophenyl 2-pentyl-1,2,3,4-tetrahydro-6-naphthoate; m.p. 72.7°–73.3° C.; cl.p. 127.7° C.

The 2-pentyl-1,2,3,4-tetrahydro-naphthalene-6-carboxylic acid used as the starting material can be prepared as follows:

(a) 51.6 g (0.456 mol) of potassium tert-butylate are added to a suspension of 178 g (0.431 mol) of n-pentyl-triphenylphosphonium bromide in 1560 ml of absolute toluene, the mixture is stirred at room temperature for 45 minutes, a solution of 41.9 g (0.287 mol) of 2-tetralone in 300 ml of absolute toluene is added dropwise thereto within 50 minutes and the mixture is heated at 75°–80° C. for 3 hours. The mixture is left to cool down and is poured into 1500 ml of ice/water. The organic phase is separated, the aqueous phase is extracted twice more with toluene and the combined toluene phases are washed with water. After drying over sodium sulphate and removing the solvent in vacuo, there are obtained 175 g of a brownish suspension which, for purification, is filtered through a column of 450 g of silica gel. Elution with hexane and benzene/hexane (1:1) yields 53.2 g of 2-pentylidene-1,2,3,4-tetrahydronaphthalene as a yellowish oil.

(b) A mixture of 53.2 g (0.268 mol) of 2-pentylidene-1,2,3,4-tetrahydronaphthalene, 275 ml of rectified alcohol, 1.4 ml of triethylamine and 1.44 g of palladium/carbon (5% by weight) is shaken at room temperature in a hydrogen atmosphere until the hydrogenation is complete (24 hours). Subsequently, the catalyst is filtered off and the solvent is removed in vacuo. The 49.4 g of 2-pentyl-1,2,3,4-tetrahydronaphthalene remaining as the residue are purified by distillation in a high vacuum; 47.3 g of a colorless liquid; b.p. 106°–110° C. (0.5 mbar).

(c) 37.6 g (0.282 mol) of anhydrous aluminium chloride are added portionwise while stirring at room temperature within 1 hour to a mixture of 47.3 g (0.234 mol) of 2-pentyl-1,2,3,4-tetrahydronaphthalene, 22.1 g (0.281 mol) of acetyl chloride and 380 ml of absolute dichloromethane, the yellow-brown mixture is boiled under reflux for 3 hours, left to stand overnight and then poured into a mixture of 500 ml of ice/water and 165 ml of concentrated hydrochloric acid. The organic layer is separated, the aqueous phase is extracted twice more with dichloromethane, the organic phases are washed with 230 ml of 3N sodium hydroxide and with water, dried over sodium sulphate and the solvent is removed in vacuo. There are obtained 57.8 g of a mixture of 2-pentyl-6-acetyl-1,2,3,4-tetrahydronaphthalene and 2-pentyl-7-acetyl-1,2,3,4-tetrahydronaphthalene as a brownish liquid which is reacted directly.

(d) A solution of 54.6 g (0.223 mol) of the mixture of 2-pentyl-6-acetyl-1,2,3,4-tetrahydronaphthalene and 2-pentyl-7-acetyl-1,2,3,4-tetrahydronaphthalene in 450 ml of dioxan is warmed to 60° C. and allowed to flow while stirring within 30 minutes into a solution of sodium hypobromite (prepared from 261 ml of 28% sodium hydroxide, 202 g of ice and 112 ml of water by the dropwise addition of 51.5 ml of bromine at 0° C. within 35 minutes). The brownish mixture is subsequently warmed to 30° C., an exothermic reaction occurring with decolorization. The mixture is left to react for a further 1 hour, the excess hypobromite is reduced by adding sodium hydrogen sulphite solution, 102 ml of concentrated hydrochloric acid are added thereto and the mixture is extracted with dichloromethane. After washing with water, drying with sodium sulphate and evaporating the solvent in vacuo, there are obtained 57.9 g of a crude mixture of 2-pentyl-1,2,3,4-tetrahydronaphthalene-6-carboxylic acid and 2-pentyl-1,2,3,4-tetrahydronaphthalene-7-carboxylic acid as a yellowish crystalline residue. The mixture of the two acids can be separated by repeated recrystallization from hexane, ethanol, isopropanol and the like. The separation of the corresponding amides (prepared in accordance with Example 10) is conducted by recrystallization from suitable solvents (e.g. acetone) and subsequent hydrolysis (e.g. with potassium hydroxide in diethyleneglycol). 2-Pentyl-1,2,3,4-tetrahydronaphthalene-6-carboxamide melts at 166.4°–167.8° C. and 2-phenyl-1,2,3,4-tetrahydronaphthalene-7-carboxamide melts at 122.9°–123.5° C. The liquid crystalline 2-pentyl-1,2,3,4-tetrahydronaphthalene-6-carboxylic acid has a melting point of 122.9°–123.1° C. and a clearing point of 174.9°–177.6° C.; the 2-pentyl-1,2,3,4-tetrahydronaphthalene-7-carboxylic acid melts at 103.6°–105.5° C. and is not liquid crystalline.

EXAMPLE 9

Preparation of 6-pentyl-trans-decalin-2-carboxylic acid p-cyanophenyl ester 1.893 g (7.50 mmol) of 6-pentyl-trans-decalin-2-carboxylic acid are boiled at reflux for 2 hours with 15 ml of thionyl chloride while excluding moisture. After removing the excess thionyl chloride in vacuo, the acid chloride is obtained as a brownish liquid.

The acid chloride, diluted with 10 ml of absolute benzene, is added dropwise while stirring at 3°–7° C. to a solution, cooled to 3° C., of 0.893 g (7.497 mmol) of p-cyanophenol in 7.5 ml of absolute pyridine, the mixture is warmed at 50°–55° C. for 3.5 hours and left to stand at room temperature overnight. The mixture is then poured into a mixture of 15 g of ice and 15 ml of hydrochloric acid (1:1), exhaustively extracted with ether and the organic phases are washed once with 11.5 ml of ice-cold 1N sodium hydroxide and with water. The crystalline residue (2.6 g) of 6-pentyl-trans-decalin-2-carboxylic acid p-cyanophenyl ester obtained after drying with sodium sulphate and removing the solvent in vacuo is, for purification, chromatographed on 90 g of silica gel. Elution with hexane/toluene and toluene yields 2.5 g of substance which is recrystallized from hexane up to a constant melting point and clearing point and dried up to constant weight in a high vacuum (0.01 mbar). There are obtained colorless crystals of the 6-pentyl-trans-decalin-2-carboxylic acid p-cyanophenyl ester; m.p. 79.9° C., cl.p. 148.0° C.

The 6-pentyl-trans-decalin-2-carboxylic acid used as the starting material can be prepared as follows:

(a) A mixture of 84.1 g (0.5 mol) of 4-pentylcyclohexanone, 51.3 g (0.72 mol) of pyrrolidine, 120 ml of toluene and 0.62 g of p-toluenesulphonic acid is heated to boiling for 2 hours while connecting a water-separator and the pyrrolidine-containing water which separates is separated off. The residue containing the 4-pentyl-1-pyrrolidinyl-1-cyclohexene is firstly freed from excess toluene in vacuo and subsequently distilled in a high vacuum; b.p. 107°–113° C. (0.16 mbar), yellowish liquid.

(b) While stirring and gassing with nitrogen there are added dropwise to a mixture of 98.4 g (0.444 mol) of 4-pentyl-1-pyrrolidinyl-1-cyclohexane and 315 ml of absolute toluene within 1 hour 35.9 g (0.512 mol) of methyl vinyl ketone (temperature increase to 42° C.). The mixture is left to stand overnight and then boiled under reflux for 3 hours. There is added to the boiling mixture a solution of 19.6 g (0.238 mol) of anhydrous sodium acetate and 39.1 ml of glacial acetic acid in 39.1 ml of water and the mixture is boiled under reflux for a further 8 hours. After cooling, the toluene layer is separated, the aqueous phases are extracted twice more with toluene and the organic phases are washed in sequence with water, 1N hydrochloric acid, water, saturated sodium hydrogen carbonate solution and water and then dried over sodium sulphate. After removing the solvent in vacuo, there is obtained a mixture of 6-pentyl-octahydro-$\Delta^{1,9}$-naphthalen-2-one and 6-pentyl-octahydro-$\Delta^{9,10}$-naphthalen-2-one as a brown liquid (106 g). For purification, the mixture is distilled in a high vacuum. Yield: 69.4 g of yellowish liquid; b.p. 127°–132° C. (0.22 mbar).

(c) A solution of 71.2 g (0.323 mol) of the aforementioned mixture of 6-pentyl-octahydro-$\Delta^{1,9}$-naphthalen-2-one and 6-pentyl-octahydro-$\Delta^{9,10}$-naphthalen-2-one in 450 ml of absolute ether is added dropwise while stirring to a solution of 17.2 g (2.479 g atoms) of lithium wire in 2 liters of liquid ammonia (dry-ice condenser), the mixture is left to react for a further 1 hour, diluted with 1 liter of absolute ether and there are added portionwise thereto 113 g (2.112 mol) of ammonium chloride until decolorization occurs. The ammonia is allowed to evaporate at room temperature overnight, the mixture is cooled with ice and made Congo-acid with concentrated hydrochloric acid. After adding water and an additional amount of ether, the ether layer is separated, the aqueous phase is extracted twice more with ether, the organic phases are washed with water and dried over sodium sulphate. After removing the solvent in vacuo, there are obtained 69.4 g of a mixture of predominantly 6-pentyl-trans-decalin-2-one and 6-pentyl-cis-decalin-2-one as a brown liquid which is used in the crude state.

(d) A solution of 23.6 g (0.482 mol) of sodium cyanide in 54 ml of water is added while gassing with nitrogen to 69.4 g (0.312 mol) of the mixture of 6-pentyl-trans-decalin-2-one and 6-pentyl-cis-decalin-2-one dissolved in 350 ml of ether. The mixture is cooled to 0° C. and there are added dropwise thereto while stirring within 2 hours 69.9 ml of 25% hydrochloric acid. Subsequently, the mixture is stirred at room temperature for a further 1 hour, the organic phase is separated, the aqueous phase is extracted twice more with ether, the combined organic phases are washed with water and dried with sodium sulphate. The cyanohydrin mixture (75.6 g of a brown oil) obtained after removing the solvent in vacuo is used in the crude state.

(e) 75.6 g (0.303 mol) of the aforementioned crude cyanohydrin mixture are dissolved while stirring in 81 ml of absolute pyridine and 67 ml of absolute benzene, cooled to $-2°$ C., treated dropwise within 20 minutes with a mixture of 42.0 ml (0.460 mol) of phosphorus oxychloride and 53.4 ml of absolute pyridine and subsequently boiled under reflux for 4 hours. The precipitate originally formed dissolves upon warming, but again forms upon cooling overnight. The mixture is poured on to 375 g of ice, diluted with ether, the ether layer is separated and the aqueous phase is extracted twice more with ether. The ether phases are washed with water, dried over sodium sulphate and freed from solvent in vacuo. There are obtained 72.5 g of a dark brown oil which consists predominantly of 6-pentyl-trans-octahydro-$\Delta^1$-naphthalene-2-carbonitrile and 6-pentyl-$\Delta^2$-naphthalene-2-carbonitrile as well as, in addition, the corresponding 9,10-cis compounds. The mixture is used in the crude state.

(f) The foregoing nitrile mixture (72.5 g, 0.313 mol) is heated at 200° C. (bath temperature) for 6.5 hours while gassing with nitrogen with a hot solution of 35.1 g (0.625 mol) of potassium hydroxide in 355 ml of diethyleneglycol. After this time, the ammonia evolution is almost complete. The mixture is left to cool, the alkaline solution, diluted with 500 ml of water, is extracted three times with ether and the organic phases are backwashed twice with water. The 17.2 g of dark brown oil obtained after drying with sodium sulphate and evaporating the ether are discarded. The aqueous phases (including water washings) are made Congo-acid with 3N sulphuric acid, a precipitate or a turbidity occurring. The mixture is exhaustively extracted with ether and the organic phases are washed with water and dried with sodium sulphate. After evaporating in vacuo, there are obtained 57.6 g of a brown, solid residue which consists predominantly of 6-pentyl-trans-octahydro-$\Delta^1$-naphthalene-2-carboxylic acid and 6-pentyl-trans-octahydro-$6\delta^2$-naphthalene-2-carboxylic acid as well as, in addition, the corresponding 9,10-cis compounds. For purification, this residue is dissolved in warm toluene and filtered through a column of 300 g of silica gel. Elution with toluene and toluene containing 1% or 2% acetone yields a total of 45.9 g of brownish, crystalline substance which is used directly.

(g) The aforementioned mixture of unsaturated acids (45.9 g) is dissolved while warming in 700 ml of rectified alcohol, cooled to room temperature and, after treatment with 4.3 g of palladium/carbon (5% by weight palladium), shaken in a hydrogen atmosphere until the hydrogenation comes to a standstill (24 hours). Subsequently, the catalyst is filtered off and the solvent is evaporated in vacuo. There are obtained 45.9 g of a yellowish crystalline residue which consists predominantly of 6-pentyl-trans-decalin-2-carboxylic acid and, in addition, still contains the cis isomer. For purification the residue is recrystallized several times from ether/hexane or hexane, the purification being followed by gas chromatography, melting point and clearing point. After sublimation in a high vacuum (0.01 mbar), there are obtained 13.7 g of pure liquid crystalline 6-pentyl-trans-decalin-2-carboxylic acid as colorless crystals; m.p. 113.5°–114.3° C., cl.p. 165.8°–167.1° C.

EXAMPLE 10

Preparation of 6-pentyl-trans-decalin-2-carbonitrile 8.95 g (35.60 mmol) of 6-pentyl-trans-decalin-2-carboxamide are suspended in 94 ml of absolute pyridine and treated while stirring with 12.94 g (73.29 mmol) of benzenesulphonyl chloride. The solution, which becomes clear, is left to stand at room temperature overnight, then poured into a mixture of 190 g of ice and 180 ml of hydrochloric acid (1:1) and exhaustively extracted with ether. The ether solutions are washed neutral with water, dried over sodium sulphate and the solvent is evaporated off in vacuo. There are obtained 11.0 g of crude 6-pentyl-trans-decalin-2-carbonitrile as a yellowish oil which crystallizes later and which, for purification, is chromatographed on 200 g of silica gel. Elution with hexane/toluene mixtures containing 30%, 40% and 50% toluene yields 8.1 g of substance which is recrystallized from hexane up to constant melting point and subsequently distilled in a high vacuum; b.p. 115°–120° C. (0.02 mbar). There is obtained 6-pentyl-trans-decalin-2-carbonitrile as colorless crystals; m.p. 41.9° C.

The 6-pentyl-trans-decalin-2-carboxyamide used as the starting material can be prepared as follows:

31.0 g (0.123 mol) of the mother liquors acid obtained in Example 9. which still contains the cis isomer in addition to 6-pentyl-trans-decalin-2-carboxylic acid, are converted into the acid chloride with 133 ml of thionyl chloride analogously to Example 9. After removing the excess thionyl chloride, it is diluted with 100 ml of absolute dichloromethane and this solution is added dropwise while stirring and cooling to a solution of 465 ml of absolute dichloromethane which is saturated with ammonia gas. Ammonia gas is introduced for a further 2.5 hours, the mixture is evaporated to dryness in vacuo, treated with 530 ml of water and 500 ml of ether and stirred at room temperature for 30 minutes. The precipitate is filtered off under suction, washed with water and ether and dried. There are obtained 8.9 g of 6-pentyl-trans-decalin-2-carboxamide which, for purification, is recrystallized from dioxan and sublimed in a high vacuum (0.01 mbar); colorless crystals, m.p. 211.6°–212.7° C. From the ether solutions there are obtained by repeated recrystallization (control by gas chromatography) a further 1.1 g of the trans amide and by recrystallization of the mother liquors from ether the 6-pentyl-cis-decalin-2-carboxamide as colorless crystals (m.p. 126.7°–128.0° C.).

EXAMPLE 11

Preparation of 2,6-dipentyl-trans-decalin

A mixture of 3.478 g (11.89 mmol) of 6-pentyl-2-valeryl-trans-decalin, 11.4 ml of absolute ethanol and 1.339 g (26.75 mmol) of hydrazine hydrate is dissolved while warming and left to stand overnight. After adding 12.2 ml of diethyleneglycol and 1.8 g (32.08 mmol) of potassium hydroxide, the mixture is heated under a descending condenser for 2 hours at 200° C. (bath temperature) and left at this temperature for 1.5 hours. The distillate and residue are combined, treated with 25 ml of water and extracted with ether. The organic phases are washed with water and dried over sodium sulphate. After evaporating the solvent in vacuo, there are obtained 3.35 g of crude 2,6-dipentyl-trans-decalin which, for purification, is chromatographed on 90 g of silica gel. Elution with hexane yields 1.74 g of substance which is distilled in a high vacuum at 145° C./0.03 mbar. There are obtained colorless crystals of 2,6-dipentyl-trans-decalin; m.p. 47.8° C.

The 6-pentyl-2-valeryl-trans-decalin used as the starting material can be prepared as follows:

A Grignard solution is prepared by the dropwise addition of a mixture of 2.890 g (21.09 mmol) of n-butyl bromide and 3.5 ml of absolute ether to a suspension of 0.513 g (21.10 mg atoms) of magnesium in 7 ml of absolute ether. After dissolution of the magnesium, there is added dropwise at 35°–37° C. while stirring a solution of 4.101 g (17.57 mmol) of 6-pentyl-trans-decalin-2-carbonitrile (prepared according to Example 10) in 7 ml of absolute ether, the mixture is boiled under reflux for 7 hours and left to stand overnight. Then there are added dropwise 3.326 g (0.104 mol) of methanol and, after stirring for 30 minutes, the precipitate formed is filtered off under suction and washed well with absolute ether. Subsequently, hydrogen chloride gas is introduced into the filtrate for 1 hour while cooling at 0° C. and the mixture is concentrated to dryness. There are obtained 6.9 g of imine hydrochloride of 6-pentyl-2-valeryl-trans-decalin as a brownish, turbid oil. This is warmed at 50° C. with 50 ml of water for 30 minutes, the 6-pentyl-2-valeryl-trans-decalin separating as an oil which later crystallizes. The mixture is extracted with ether, the organic phase is washed with water, dried over sodium sulphate and the solvent is removed in vacuo. There remain 5.3 g of brownish, crystallizing oil which, for purification, can be recrystallized (e.g. from hexane). There are thus obtained colorless crystals of 6-pentyl-2-valeryl-trans-decalin; m.p. 47.0°–48.5° C.

EXAMPLE 12

Preparation of 2-pentyl-1,3-benzodioxan-6-carboxylic acid p-propylpehnyl ester 0.1 g of 4-(dimethylamino)pyridine and 1.6 g of p-propylphenol are added to a solution of 2.5 g of 2-pentyl-1,3-benzodioxan-6-carboxylic acid in 50 ml of methylene chloride. The mixture is treated portionwise at 0° C. while stirring with 2.4 g of N,N'-dicyclohexylcarbodiimide. After completion of the addition, the mixture is stirred at 0° C. for a further 10 minutes and then at room temperature for 3 hours. The precipitate is filtered off and the filtrate is evaporated. The residue is taken up in 40 ml of methylene chloride and again filtered. The filtrate is washed with saturated sodium carbonate solution and then with water, dried over sodium sulphate, filtered and evaporated. The crude product is dissolved in boiling hexane, filtered hot with active carbon and crystallized from the filtrate. The crystallizate is recrystallized twice more from hexane. There is obtained pure 2-pentyl-1,3-benzodioxan-6-carboxylic acid p-propylphenyl ester; m.p. 97.5° C., cl.p. 74.5° C. (monotropic).

The 2-pentyl-1,3-benzodioxan-6-carboxylic acid used as the starting material can be prepared as follows:

A mixture of 16.8 g of 4-hydroxy-3-(hydroxymethyl)-benzoic acid, 1000 ml of benzene, 15.0 g of caproaldehyde and 0.36 ml of concentrated sulphuric acid is boiled for 5 hours while stirring under a water separator. After cooling, the mixture is filtered. The filtrate is concentrated and the residue is boiled up with hexane. The insoluble material is dissolved in ether/hexane and stirred up in the cold with active carbon. The mixture is filtered, the filtrate is evaporated and the residue is boiled with isopropyl ether. There are obtained 11.7 g of beige colored 2-pentyl-1,3-benzodioxan-6-carboxylic acid; m.p. 148° C.

EXAMPLE 13

Preparation of 2-pentyl-1,3-benzodioxan-6-carbonitrile 1.85 ml of benzenesulphonyl chloride are added dropwise while stirring to a suspension of 1.2 g of 2-pentyl-1,3-benzodioxan-6-carboxamide in 10 ml of pyridine. The mixture is left to stand overnight and then the solution is extracted with 15 ml of 1N sodium hydroxide and ether. The aqueous phase is separated and back-extracted with ether. The combined organic phase is washed with 1N sodium hydroxide and then with water, dried over sodium sulphate, filtered and concentrated. The residue is treated with hot hexane. The mixture is decanted off from insoluble material and the solution is evaporated. The crude product is recrystallized once from hexane and twice from isopropanol. There is obtained 2-pentyl-1,3-benzodioxan-6-carbonitrile; m.p. 40.5°–41° C. (not liquid crystalline).

The 2-pentyl-1,3-benzodioxan-6-carboxamide used as the starting material can be prepared as follows:

A mixture of 3.0 g of 2-pentyl-1,3-benzodioxan-6-carboxylic acid (prepared in accordance with Example 12), 60 ml of chloroform and 2.2 ml of triethylamine is cooled to 0° C. 1.5 ml of ethyl chloroformate are added dropwise while stirring. The mixture is stirred at 0° C. for 1 hour and then ammonia gas is conducted in. The mixture is stirred at room temperature for 5 hours and then evaporated. The residue is stirred up with 100 ml of water and the suspension is suction filtered. The material on the suction filter is dried and boiled up with hexane. There is obtained 2-pentyl-1,3-benzodioxan-6-carboxamide as a beige powder; m.p. 162.5°–163° C.

EXAMPLE 14

Preparation of 2-pentyl-6-propyl-1,3-benzodioxan 2.5 g of crude 2-pentyl-6-propenyl-1,3-benzodioxan are dissolved in 75 ml of ethanol and hydrogenated with 0.25 g of palladium/carbon (5% by weight) at room temperature until the hydrogen uptake comes to a standstill. The mixture is filtered and concentrated. The crude product is purified by chromatography on a column of 32 g of basic aluminium oxide with hexane/ether (9:1). Pure 2-pentyl-6-propyl-1,3-benzodioxan is obtained as a colorless oil.

The 2-pentyl-6-propenyl-1,3-benzodioxan used as the starting material can be prepared as follows:

(a) A solution of 10.0 g of 2-pentyl-1,3-benzodioxan-6-carboxylic acid (prepared in accordance with Example 12) in 400 ml of ether is added to a suspension of 1.6 g of lithium aluminium hydride in 400 ml of dry ether in such a manner that the hydrogen evolution can be held under control. The mixture is stirred at room temperature for a further 1 hour and then 50 ml of acetone and 100 ml of water are added thereto cautiously. The aqueous phase is separated and back-extracted with ether. The combined organic phase is washed with water, dried over sodium sulphate and evaporated. 8.7 g of 2-pentyl-1,3-benzodioxan-6-carbinol is obtained as a colorless oil.

(b) A solution of 8.5 g of 2-pentyl-1,3-benzodioxan-6-carbinol in 225 ml of toluene is added to 13 g of activated manganese dioxide. The mixture is heated to boiling overnight and then filtered. After rinsing with a small amount of toluene, the filtrate is concentrated at 50° C. on a rotary evaporator. 8.0 g of crude 2-pentyl-1,3-benzodioxan-6-carboxaldehyde are obtained as a yellowish oil.

(c) A mixture of 4.8 g of 2-pentyl-1,3-benzodioxan-6-carboxaldehyde, 100 ml of dioxan, 5 g of finely powdered potassium carbonate and 11.5 g of ethyltriphenylphosphonium bromide is heated to boiling under reflux for 24 hours. The inorganic salts are filtered off and back-washed with dioxan and the filtrate is evaporated. The residue is stirred up with hexane. Insoluble triphenylphosphine oxide is filtered off and the filtrate is evaporated. The residue is distilled at 210° C./11 mmHg in a bulb-tube. The turbid distillate is re-distilled at 130° C./0.1 mmHg in a bulb-tube. 2.5 g of crude, oily 2-pentyl-6-propenyl-1,3-benzodioxan are obtained.

We claim:

1. A compound of the formula:

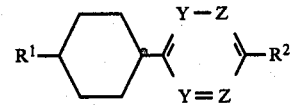

wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl; where each alkyl denotes either a straight chain alkyl group of 1 to 12 carbon atoms or a branched chain alkyl group of the formula $C_2H_5$—$CH(CH_3)$—$(CH_2)_n$, n is 1, 2 or 3; with the proviso that the compound contains at most only one of said branched chain alkyl group and with the further proviso that the sum of the carbon atoms in all of the alkyl groups within the compound is at most 14.

2. The compound of claim 1 wherein Y is nitrogen and Z is =CH—.

3. The compound of claim 2 wherein $R^2$ is cyano.

4. The compound of claim 3 wherein $R^1$ is said straight chain alkyl group.

5. The compound of claim 4 wherein said straight chain alkyl group for $R^1$ has 2 to 7 carbon atoms.

6. The compound of claim 3, trans-2-(4-propylcyclohexyl)-5-pyrimidinecarbonitrile.

7. The compound of claim 3, trans-2-(4-methylcyclohexyl)-5-pyrimidinecarbonitrile.

8. The compound of claim 3, trans-2-(4-ethylcyclohexyl)-5-pyrimidinecarbonitrile.

9. The compound of claim 3, trans-2-(4-butylcyclohexyl)-5-pyrimidinecarbonitrile.

10. The compound of claim 3, trans-2-(4-pentylcyclohexyl)-5-pyrimidinecarbonitrile.

11. The compound of claim 2 wherein $R^2$ is said straight chain alkyl group.

12. The compound of claim 11 wherein said straight chain alkyl group for $R^2$ has 2 to 7 carbon atoms.

13. The compound of claim 12 wherein $R^1$ is said straight chain alkyl group.

14. The compound of claim 13 wherein said straight chain alkyl group for $R^1$ has 2 to 7 carbon atoms.

15. The compound of claim 14, trans-2-(4-pentylcyclohexyl)-5-heptylpyrimidine.

16. The compound of claim 14, trans-2-(4-propylcyclohexyl)-5-propylpyrimidine.

17. The compound of claim 14, trans-2-(4-propylcyclohexyl)-5-butylpyrimidine.

18. The compound of claim 14, trans-2-(4-pentylcyclohexyl)-5-propylpyrimidine.

19. The compound of claim 14, trans-2-(4-pentylcyclohexyl)-5-butylpyrimidine.

20. The compound of claim 14, trans-2-(4-pentylcyclohexyl)-5-pentylpyrimidine.

21. The compound of claim 14, trans-2-(4-heptylcyclohexyl)-5-heptylpyrimidine.

22. The compound of claim 2 wherein $R^2$ is p-alkylphenyl.

23. The compound of claim 22 wherein the alkyl in said p-alkylphenyl is said straight chain alkyl group.

24. The compound of claim 23 wherein said straight chain alkyl group in p-alkylphenyl has 2 to 7 carbon atoms.

25. The compound of claim 22 wherein $R^1$ is said straight chain alkyl group.

26. The compound of claim 25 wherein said straight chain alkyl group for $R^1$ has 2 to 7 carbon atoms.

27. The compound of claim 26, trans-2-(4-pentylcyclohexyl)-5-(p-butylphenyl)pyrimidine.

28. The compound of claim 26, trans-2-(4-propylcyclohexyl)-5-(p-butylphenyl)pyrimidine.

29. The compound of claim 2 wherein $R^2$ is trans-4-alkylcyclohexyl.

30. The compound of claim 29 wherein the alkyl in said trans-4-alkylcyclohexyl is said straight chain alkyl group.

31. The compound of claim 29 wherein $R^1$ is said straight chain alkyl group.

32. The compound of claim 1 wherein Z is nitrogen and Y is =CH—.

33. The compound of claim 32 wherein $R^2$ is cyano.

34. The compound of claim 33 wherein $R^1$ is said straight chain alkyl group.

35. The compound of claim 34 wherein said straight chain alkyl group for $R^1$ has 2 to 7 carbon atoms.

36. The compound of claim 35, trans-5-(4-pentylcyclohexyl)-2-pyrimidinecarbonitrile.

37. The compound of claim 35, trans-5-(4-heptylcyclohexyl)-2-pyrimidinecarbonitrile.

38. The compound of claim 33 wherein $R^1$ is said branched chain alkyl group.

39. The compound of claim 38, (+)-trans-5-[4-(2-methylbutyl)cyclohexyl]-2-pyrimidinecarbonitrile.

40. The compound of claim 32 wherein $R^2$ is said straight chain alkyl group.

41. The compound of claim 40 wherein said straight chain alkyl group for $R^2$ has 2 to 7 carbon atoms.

42. The compound of claim 40 wherein $R^1$ is said straight chain alkyl group.

43. The compound of claim 42 wherein said straight chain alkyl group for $R^1$ has 2 to 7 carbon atoms.

44. The compound of claim 43, trans-5-(4-propylcyclohexyl)-2-pentylpyrimidine.

45. The compound of claim 43, trans-5-(4-ethylcyclohexyl)-2-pentylpyrimidine.

46. The compound of claim 43, trans-5-(4-propylcyclohexyl)-2-propylpyrimidine.

47. The compound of claim 43, trans-5-(4-propylcyclohexyl)-2-butylpyrimidine.

48. The compound of claim 43, trans-5-(4-pentylcyclohexyl)-2-propylpyrimidine.

49. The compound of claim 43, trans-5-(4-pentylcyclohexyl)-2-butylpyrimidine.

50. The compound of claim 43, trans-5-(4-pentylcyclohexyl)-2-pentylpyrimidine.

51. The compound of claim 43, trans-5-(4-heptylcyclohexyl)-2-propylpyrimidine.

52. The compound of claim 43, trans-5-(4-heptylcyclohexyl)-2-butylpyrimidine.

53. The compound of claim 43, trans-5-(4-heptylcyclohexyl)-2-pentylpyrimidine.

54. The compound of claim 32 wherein $R^2$ is p-alkylphenyl.

55. The compound of claim 54 wherein the alkyl in said p-alkylphenyl is said straight chain alkyl group.

56. The compound of claim 55 wherein said straight chain alkyl group in said p-alkylphenyl has 2 to 7 carbon atoms.

57. The compound of claim 55 wherein $R^1$ is said straight chain alkyl group.

58. The compound of claim 57 wherein said straight chain alkyl group for $R^1$ has 2 to 7 carbon atoms.

59. The compound of claim 58, trans-5-(4-propylcyclohexyl)-2-(p-pentylphenyl)pyrimidine.

60. The compound of claim 58, trans-5-(4-ethylcyclohexyl)-2-(p-propylphenyl)pyrimidine.

61. The compound of claim 58, trans-5-(4-ethylcyclohexyl)-2-(p-butylphenyl)pyrimidine.

62. The compound of claim 58, trans-5-(4-ethylcyclohexyl)-2-(p-pentylphenyl)pyrimidine.

63. The compound of claim 58, trans-5-(4-ethylcyclohexyl)-2-(p-heptylphenyl)pyrimidine.

64. The compound of claim 58, trans-5-(4-propylcyclohexyl)-2-(p-propylphenyl)pyrimidine.

65. The compound of claim 58, trans-5-(4-pentylcyclohexyl)-2-(p-propylphenyl)pyrimidine.

66. The compound of claim 58, trans-5-(4-pentylcyclohexyl)-2-(p-butylphenyl)pyrimidine.

67. The compound of claim 58, trans-5-(4-heptylcyclohexyl)-2-(p-ethylphenyl)pyrimidine.

68. The compound of claim 58, trans-5-(4-heptylcyclohexyl)-2-(p-pentylphenyl)pyrimidine.

69. The compound of claim 32 wherein $R^2$ is trans-4-alkylcyclohexyl.

70. The compound of claim 69 wherein the alkyl group in said trans-4-alkylcyclohexyl is said straight chain alkyl group.

71. The compound of claim 70 wherein said straight chain alkyl group in said trans-4-alkylcyclohexyl has 2 to 7 carbon atoms.

72. The compound of claim 70 wherein said straight chain alkyl group for $R^1$ has 2 to 7 carbon atoms.

73. The compound of claim 72 wherein said straight chain alkyl group for $R^1$ has 2 to 7 carbon atoms.

74. The compound of claim 73, 5-(trans-4-propylcyclohexyl)-2-(trans-4-pentylcyclohexyl)pyrimidine.

75. The compound of claim 73, 5-(trans-4-heptylcyclohexyl)-2-(trans-4-pentylcyclohexyl)pyrimidine.

76. The compound of claim 1 wherein Y is nitrogen; Z is =CH—; $R^1$ is alkyl and $R^2$ is cyano, alkyl, p-alkylphenyl or trans-4-alkylcyclohexyl, where each alkyl denotes a straight chain alkyl group of 2 to 7 carbon atoms; with the proviso that the sum of the carbon atoms in all the alkyl groups within the compound is at most 14.

77. The compound of claim 1 wherein Y is nitrogen; Z is =CH—, $R^1$ and $R^2$ each are a straight chain alkyl group of 2 to 7 carbon atoms.

78. The compound of claim 1 wherein Z is nitrogen; Y is =CH—; $R^1$ is alkyl and $R^2$ is cyano, alkyl, p-alkylphenyl or trans-4-alkylcyclohexyl, where each alkyl denotes a straight chain alkyl group of 2 to 7 carbon atoms; with the proviso that the sum of the carbon atoms in all of the alkyl groups within the compound is at most 14.

79. The compound of claim 1 wherein Z is nitrogen; Y is =CH—; $R^1$ is alkyl; and $R^2$ is p-alkylphenyl or cyano; where each alkyl denotes a straight chain alkyl group of 2 to 7 carbon atoms with the proviso that the sum of the carbon atoms in all of the alkyl groups within the compound is at most 14.

80. An electro-optical cell containing a liquid crystalline mixture comprising at least one compound of the formula:

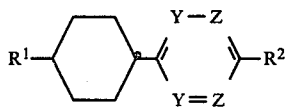

I wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl; where each alkyl denotes either a straight chain alkyl group of 1 to 12 carbon atoms or a branched chain alkyl group of the formula $C_2H_5$—$CH(CH_3)$—$(CH_2)_n$, n is 1, 2 or 3; with the proviso that the compound contains at most only one of said branched chain alkyl group and with the further proviso that the sum of the carbon atoms in all of the alkyl groups within the compound is at most 14.

81. A liquid crystalline mixture comprising at least one compound of the formula:

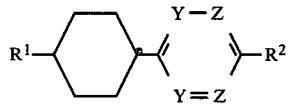

I wherein Y is nitrogen and Z is =CH—, or Z is nitrogen and Y is =CH—; $R^1$ is alkyl and $R^2$ is cyano, alkyl, p-alkylphenyl or trans-4-alkylcyclohexyl; where each alkyl denotes either a straight chain alkyl group of 1 to 12 carbon atoms or a branched alkyl group of the formula $C_2H_5$—$CH(CH_3)$—$(CH_2)_n$, n is 1, 2 or 3; with the proviso that the compound contains at most only one of said branched chain alkyl group and with the further proviso that the sum of the carbon atoms in all of the alkyl groups within the compound is at most 14.

82. The liquid crystalline mixture of claim 81 further comprising a compound of the formula:

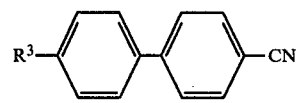

II wherein $R^3$ is a straight chain alkyl or alkoxy group of 2 to 7 carbon atoms.

83. The liquid crystalline mixture of claim 81 further comprising at least one compound of the formula:

III wherein $R^4$ is a straight chain alkyl group of 3 to 7 carbon atoms.

84. The liquid crystalline mixture of claim 81 further comprising at least one compound of the formula:

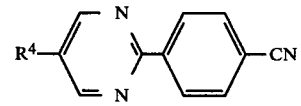

IV wherein $R^4$ is a straight chain alkyl group of 3 to 7 carbon atoms.

85. The liquid crystalline mixture of claim 81 further comprising at least one compound of the formula:

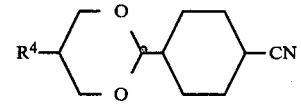

V wherein $R^4$ is a straight chain alkyl group of 2 to 7 carbon atoms.

86. The liquid crystalline mixture of claim 81 further comprising at least one compound of the formula:

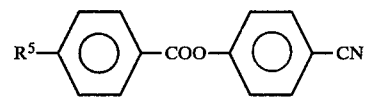

VI wherein $R^5$ is straight chain alkyl group of 2 to 7 carbon atoms.

87. The liquid crystalline mixture of claim 81 further comprising at least one compound of the formula:

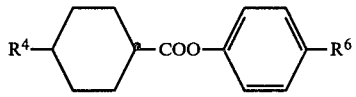

VII wherein $R^4$ is a straight chain alkyl group of 2 to 7 carbon atoms and $R^6$ is cyano or a straight chain alkoxy group of 1 to 3 carbon atoms.

88. The liquid crystalline mixture of claim 81 further comprising at least one compound of the formula:

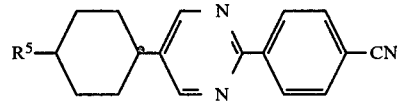

VIII wherein $R^5$ is a straight chain alkyl group of 2 to 7 carbon atoms.

* * * * *